United States Patent [19]
Bonutti et al.

[11] Patent Number: 5,514,143
[45] Date of Patent: May 7, 1996

[54] APPARATUS AND METHOD FOR USE DURING SURGERY

[75] Inventors: Peter M. Bonutti, Effingham; Gary E. Zitzmann, Newton, both of Ill.

[73] Assignee: Apogee Medical Products, Inc., Effingham, Ill.

[21] Appl. No.: 799,560

[22] Filed: Nov. 27, 1991

[51] Int. Cl.⁶ .................................................. A61F 5/00
[52] U.S. Cl. ............................ 606/86; 606/79; 606/88
[58] Field of Search .............................. 66/86, 87, 88, 66/79, 82; 623/18, 39; 128/882

[56] References Cited

U.S. PATENT DOCUMENTS

| | | |
|---|---|---|
| 1,920,821 | 8/1933 | Wassenaar . |
| 4,220,146 | 9/1980 | Cloutier . |
| 4,349,018 | 9/1982 | Chambers . |
| 4,457,307 | 7/1984 | Stillwell .................................. 606/88 |
| 4,487,203 | 12/1984 | Androphy . |
| 4,501,266 | 2/1985 | McDaniel . |
| 4,524,766 | 6/1985 | Petersen . |
| 4,567,886 | 2/1986 | Petersen ............................ 128/92 H |
| 4,574,994 | 11/1986 | Cook ...................................... 606/88 |
| 4,624,250 | 11/1986 | Saunders et al. . |
| 4,703,751 | 11/1987 | Pohl . |
| 4,712,542 | 12/1987 | Daniel et al. . |
| 4,738,253 | 4/1988 | Buechel et al. ................... 128/92 V W |
| 4,787,383 | 11/1988 | Kenna ................................... 606/88 |
| 4,825,857 | 5/1989 | Kenna . |
| 4,901,711 | 2/1990 | Goble et al. . |
| 4,938,762 | 7/1990 | Wehrli . |
| 4,968,316 | 11/1990 | Hergenroeder . |
| 5,002,547 | 3/1991 | Poggie .................................... 606/88 |
| 5,007,912 | 4/1991 | Albrektsson et al. . |
| 5,021,056 | 6/1991 | Hofman ................................ 606/86 |

OTHER PUBLICATIONS

The P.C.A. Primary Total Knee System—Alignment Rationale.
The P.C.A. Primary Total Knee System—Surgical Technique.

*Primary Examiner*—Michael A. Brown
*Attorney, Agent, or Firm*—Tarolli, Sundheim, Covell, Tummino & Szabo

[57] ABSTRACT

An improved apparatus provided to position the femur and tibia of a leg relative to each other during surgery includes a femoral section which is fixedly mounted on the femur and a tibial section which is fixedly mounted on the tibia. The femoral and tibial sections are movable relative to each other during bending of the leg. An index assembly is provided to interconnect the femoral and tibial sections when the femur and tibia are in any one of a plurality of predetermined orientations relative to each other. A pair of cams and cam followers are provided on opposite sides of the leg to support and guide movement of the femur and tibia relative to each other during bending of the leg. The cams have surfaces with configurations which are a function of the relative movement between the femur and tibia during bending of the leg. The cams and cam followers can be used to effect distraction of the knee joint and to maintain the extent of distraction of the knee joint constant during bending of the leg. The medial and lateral portions of the knee joint may have different extents of distraction.

137 Claims, 11 Drawing Sheets

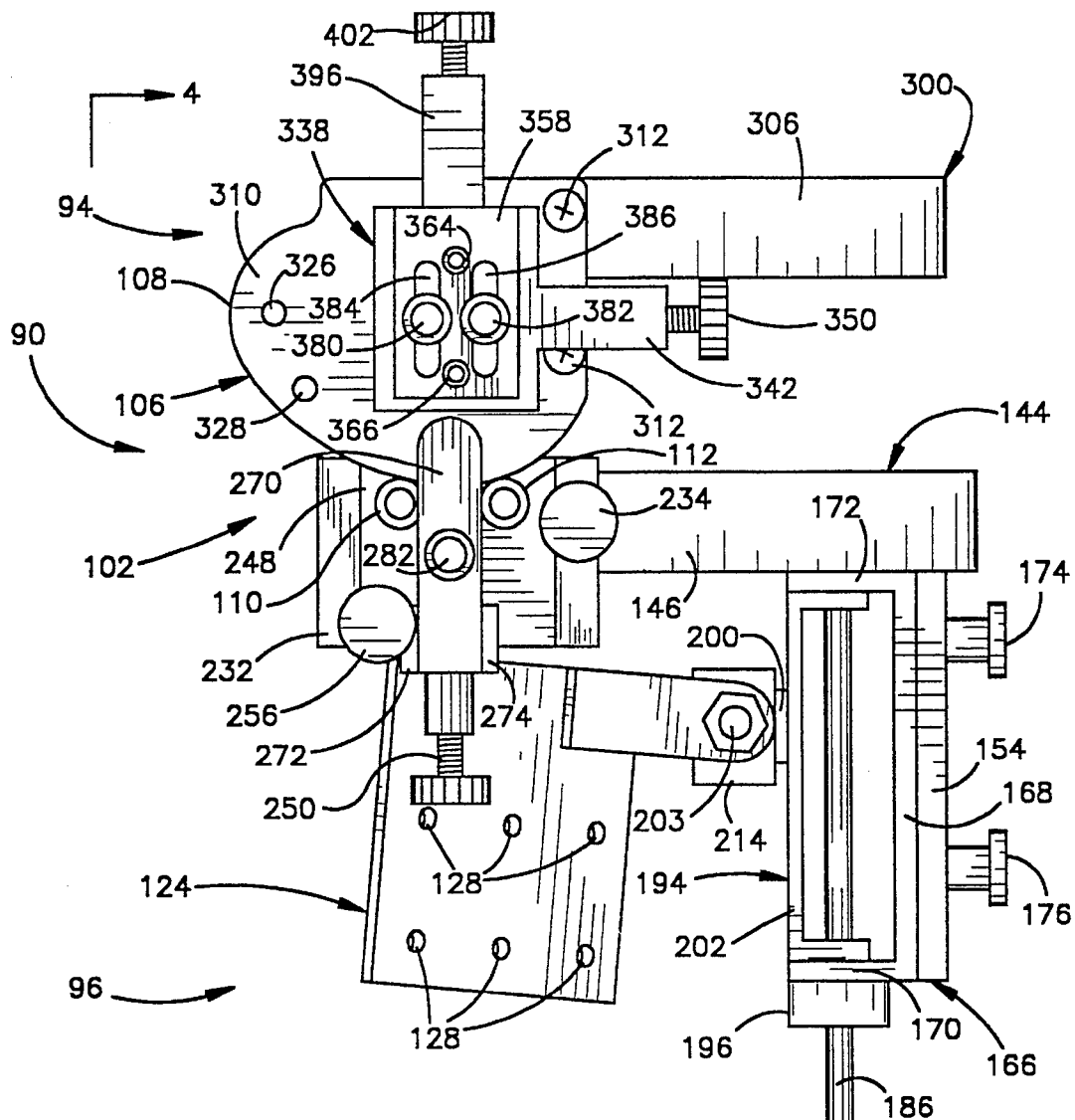
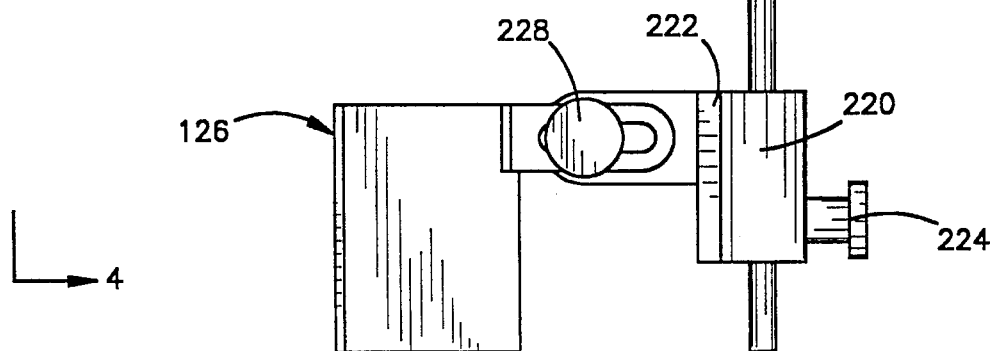
Fig.3

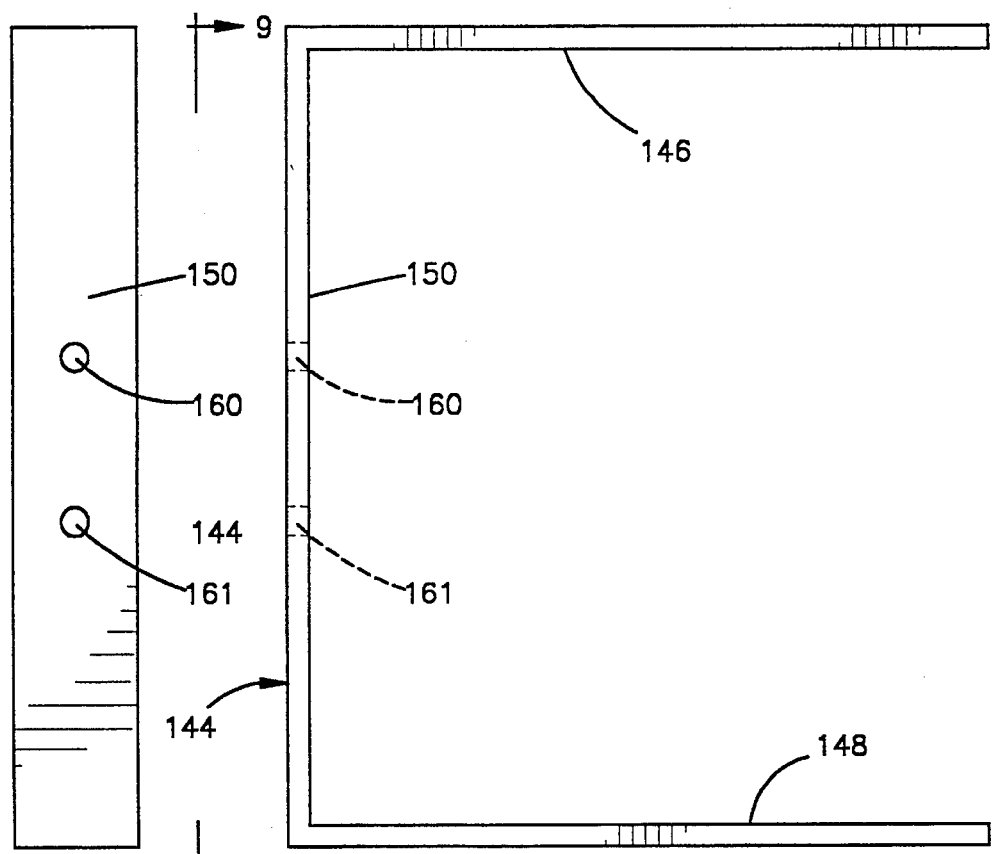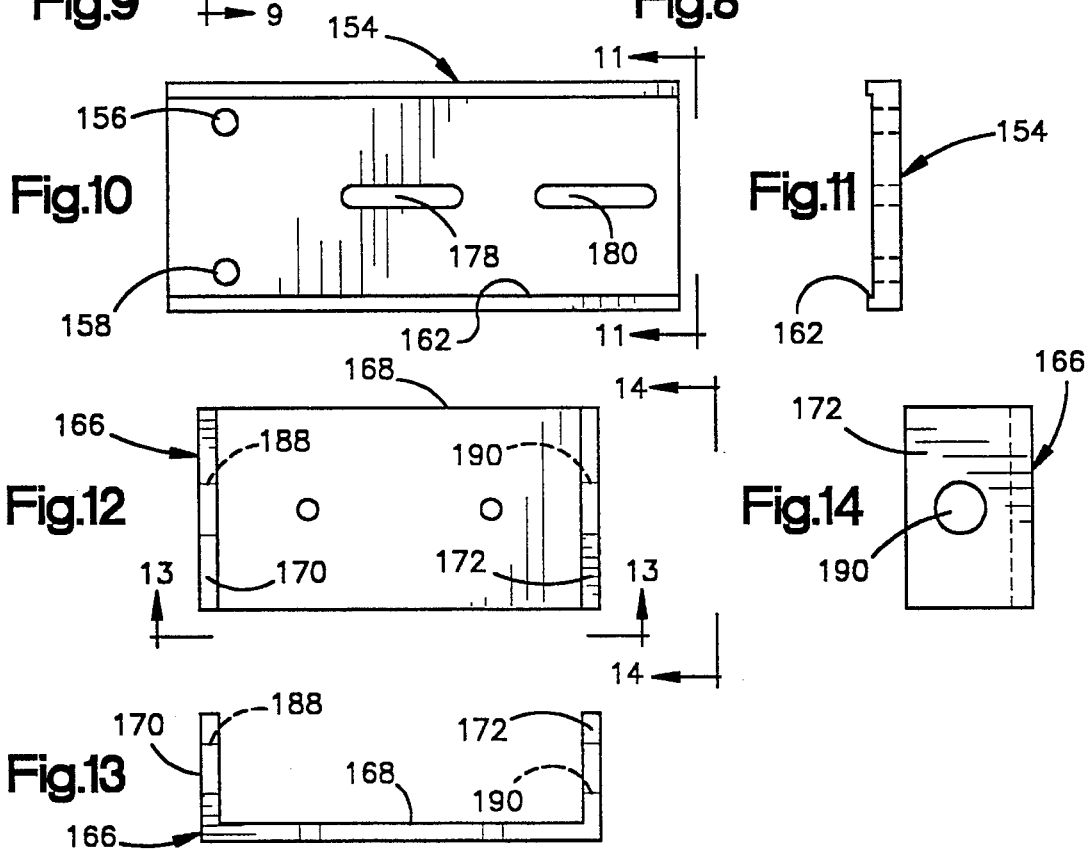

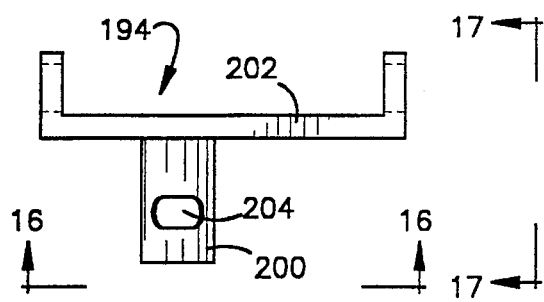
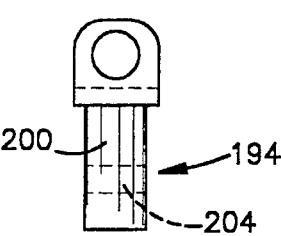
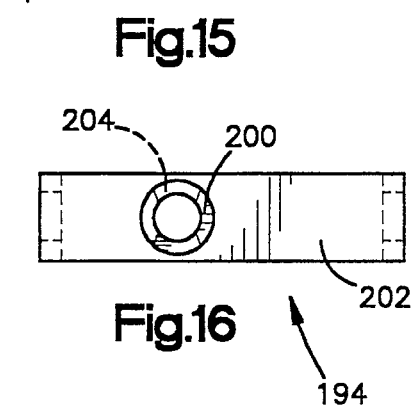
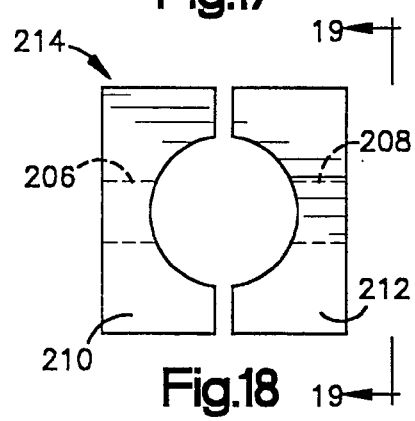
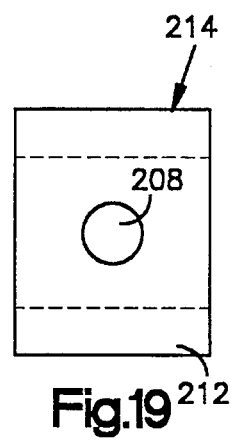
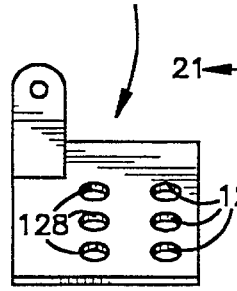
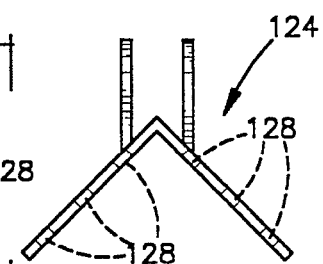
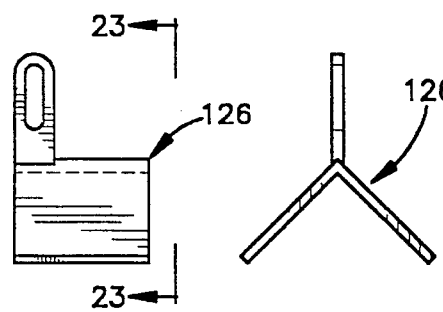
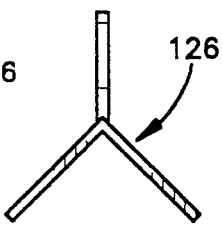
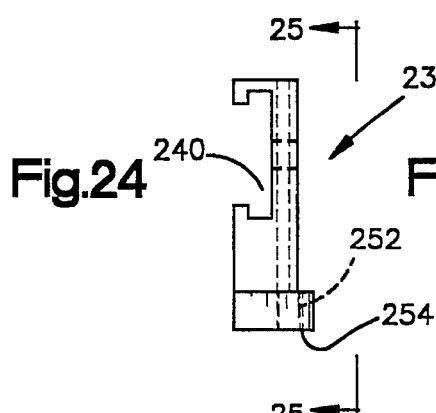
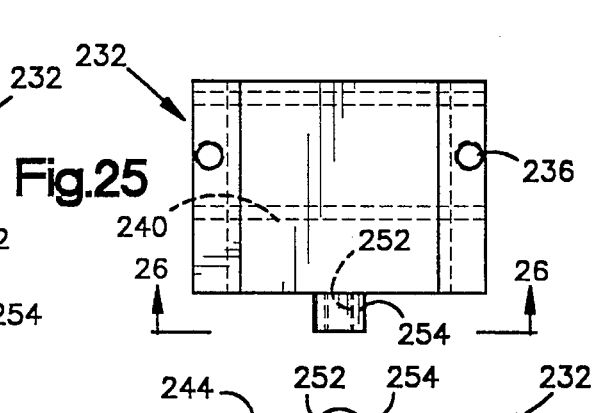

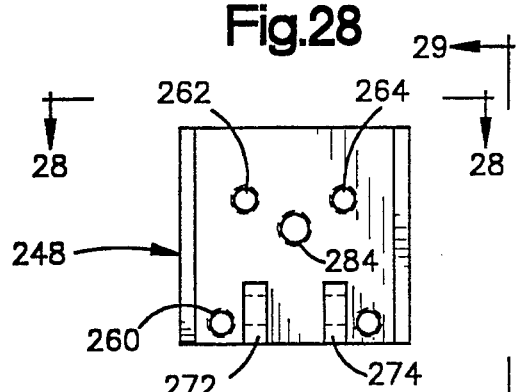
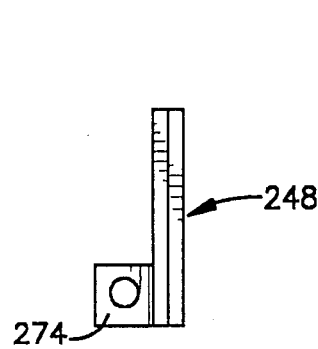
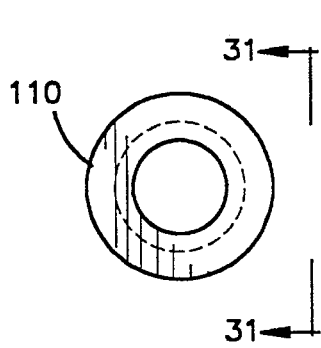
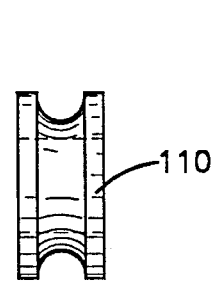
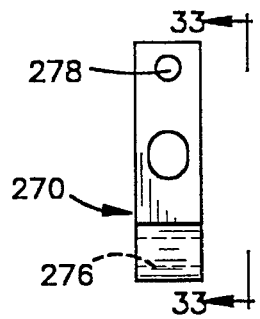
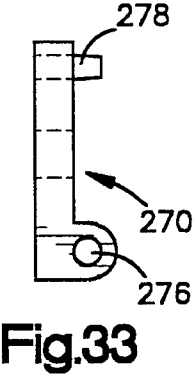
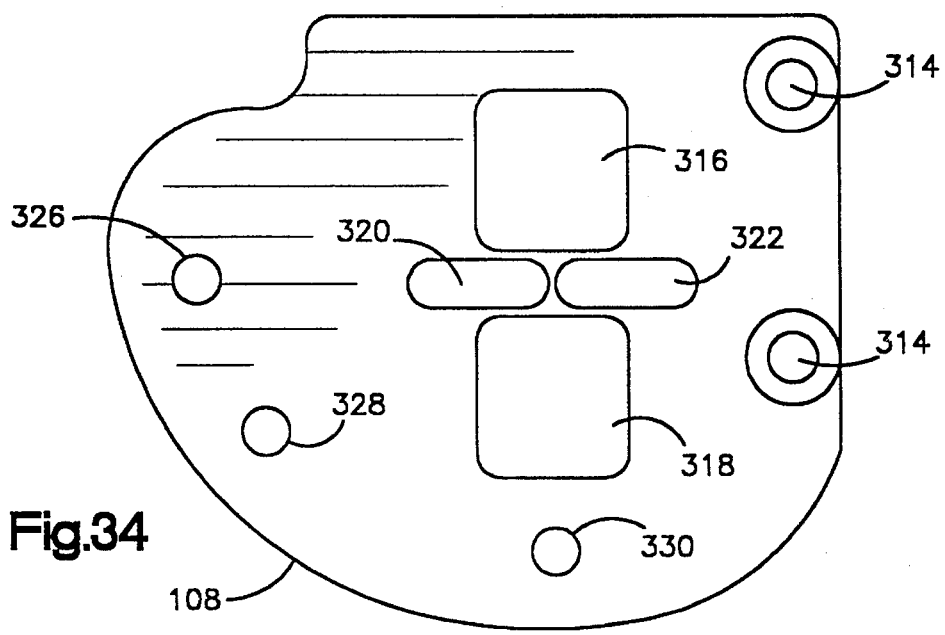

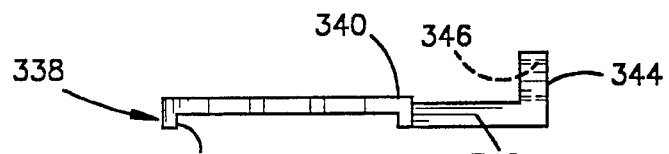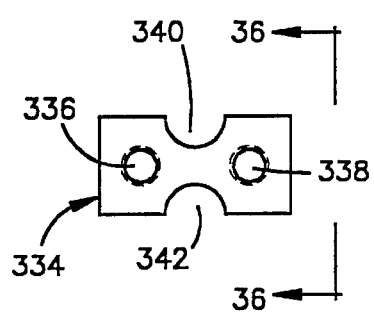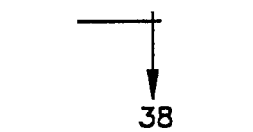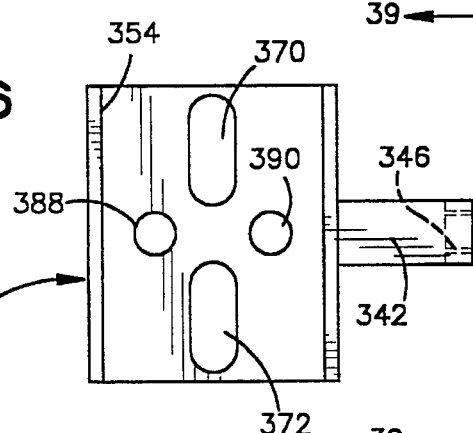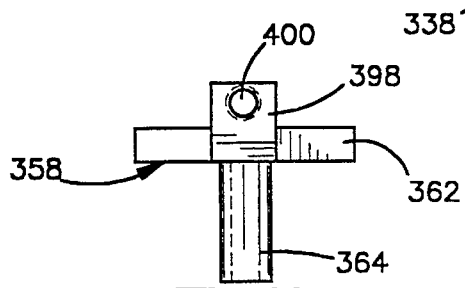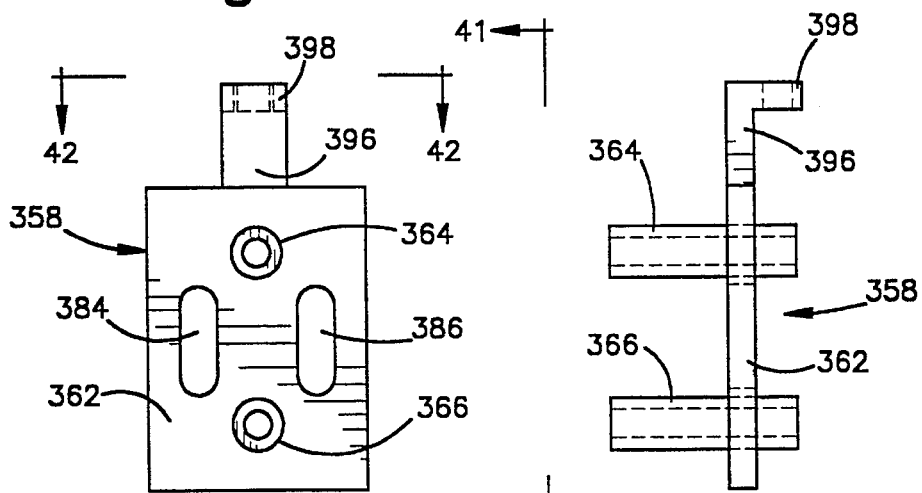

APPARATUS AND METHOD FOR USE DURING SURGERY

BACKGROUND OF THE INVENTION

The present invention relates to a new and improved apparatus and method for use in positioning the femur and tibia of a leg relative to each other during surgery.

Although the apparatus and method of the present invention can be utilized during surgery in which a total knee replacement is undertaken, it is believed that the apparatus and method will be particularly advantageous for use during arthroscopic surgery in which unicompartmental knee replacement is undertaken. Using known apparatus and methods, surgeons tend to avoid unicompartmental knee replacement because of the accuracy with which bone cuts should be made and the time required to perform the surgery.

A known unicompartmental knee replacement system does not link the femur and tibia during surgery. Therefore, the surgeon makes his cuts independently and cannot obtain reproducible alignment of the femur and tibia. In addition, distraction of the joint cannot be obtained to correct for defects in the joint and to open the joint to facilitate surgery. This known system does not provide for correction of the transverse axis and/or mechanical axis of the joint.

A known system for unicompartmental knee replacement requires bone cuts to be made from the femoral component at 0°, 45° and 90° of leg flexion. Separate alignment, soft tissue balancing and measurement of each cut is required to determine the appropriate depth of cut. This is extremely time-consuming and very surgeon dependent. This procedure has been known to take over seven hours, even for a highly trained surgeon. This does not allow for tourniquet time or for any potential for the average or above average arthroscopic surgeon to perform such a difficult and time-consuming procedure.

The known system for unicompartmental knee replacement does not provide for distraction of the joint and appropriate restoration of the mechanical axis during surgery. Distraction of the joint is critical for improved visualization and for appropriate ligament balancing and releases. The aforementioned and other difficulties have resulted in surgeons tending to avoid unicompartmental knee replacements.

Although surgeons have, in the past, tended to avoid unicompartmental knee replacements, there are factors which favor this system. It is believed that a unicompartmental knee replacement provides for early rehabilitation of a patient with less trauma and pain. This will result in the patient's hospital stay being significantly shortened. In addition, scarring, adhesions and post-operative complications, which are common with open arthrotomy approaches, are avoided.

SUMMARY OF THE INVENTION

The present invention provides a new and improved apparatus and method for use in positioning the femur and tibia of a leg relative to each other during surgery. The apparatus and method are advantageously used during unicompartmental knee replacements in order to overcome the aforementioned problems. However, the apparatus and method can be used during other surgical procedures on many different parts of the body.

The apparatus includes a femoral section which is connected with the femur for movement therewith. A tibial section is connected with the tibia for movement therewith. The two sections are movable relative to each other during flexion or extension of the leg.

An index assembly is provided to retain the femoral and tibial sections in any one of a plurality of predetermined orientations relative to each other during surgery. Since the femur and tibia can be held in any one of a plurality of predetermined orientations during surgery, there is reproducible alignment of the femur and tibia at each of the predetermined orientations to facilitate the making of accurate cuts during surgery. It is believed that this will avoid many of the problems which have been encountered in using known unicompartmental knee replacement systems. However, the method and apparatus of the present invention will also be useful during other surgical procedures.

The apparatus includes a cam which cooperates with the followers to support and position the femur and tibia during flexion or extension of the leg. The cam has a surface with a configuration which is a function of the relative movement which naturally occurs between the femur and tibia during bending movement of the leg. Therefore, the cam cooperates with the cam followers to support and position the femur and tibia for natural movement relative to each other as the leg is moved during surgery.

In addition, the cam and followers cooperate with each other to effect distraction of a knee joint interconnecting the femur and tibia. Thus, the cam and followers can be adjusted to transmit force which separates the end portions of the femur and tibia. The cam and followers cooperate to maintain the extent of separation of the end portions of the femur and tibia constant during movement of the leg. The extent of distraction of the medial portion of the knee can be different than the extent of distraction of the lateral portion of the knee if desired. However, the extent of distraction of both portions of the knee is kept constant as the leg is moved. This enables the normal mechanical transverse axis of the knee to be established during surgery.

It is contemplated that the apparatus and method of the invention will be used in conjunction with surgery on many different parts of the body. Thus, it is believed that the concepts relating to joint distraction may be used in conjunction with surgery on fingers, ankles or toes. It is also believed that the concepts relating to positioning of one part of a body relative to another may be used in conjunction with surgery on fingers, ankles, or toes.

BRIEF DESCRIPTION OF THE DRAWINGS

The foregoing and other features of the present invention will become more apparent upon a consideration of the following description taken in connection with the accompanying drawings, wherein:

FIG. 3 is a side elevational view of an alignment jig assembly constructed in accordance with the present invention to position a femur and tibia of a leg relative to each other during surgery;

FIG. 8 is a plan view of a saddle used in a tibial section of the alignment jig assembly of FIGS. 3 and 4;

FIG. 9 a view taken generally along the line 9—9 of FIG. 8;

FIG. 10 is a plan view of a tibial slide used in the tibial section of the alignment jig assembly of FIGS. 3 and 4;

FIG. 11 is a view taken generally along the line 11—11 of FIG. 10;

FIG. 12 is a plan view of a mounting bracket used in the tibial section of the alignment jig assembly;

FIG. 13 is a view taken generally along the line 13—13 of FIG. 12;

FIG. 14 is a view taken generally along the line 14—14 of FIG. 12;

FIG. 15 is a side elevational view of a swivel plate used in the tibial section of the alignment jig assembly;

FIG. 16 is a view taken generally along the line 16—16 of FIG. 15;

FIG. 17 is a view taken generally along the line 17—17 of FIG. 15;

FIG. 18 is a plan view of a split clamp used in the tibial section of the alignment jig assembly;

FIG. 19 is a view taken generally along line 19—19 of FIG. 18;

FIG. 20 is a side elevational view of a tibial locating and mounting bracket used in the tibial section of the alignment jig assembly;

FIG. 21 is a view taken along the line 21—21 of FIG. 20;

FIG. 22 is a side elevational view of an ankle bracket used in the tibial section of the alignment jig assembly;

FIG. 23 is a view taken along the line 23—23 of FIG. 22;

FIG. 24 is an elevational view of a cam follower adjustment block utilized in the tibial section of the alignment jig assembly;

FIG. 25 is a view taken along the line 25—25 of FIG. 24;

FIG. 26 is a view taken along the line 26—26 of FIG. 25;

FIG. 27 is a plan view of a cam follower guide block utilized in the tibial section of the alignment jig assembly;

FIG. 28 is a view along the line 28—28 of FIG. 27;

FIG. 29 is a view along the line 29—29 of FIG. 27;

FIG. 30 is a plan view of a cam follower roller used in the tibial section of the alignment jig assembly;

FIG. 31 is a view taken along the line 31—31 of FIG. 30;

FIG. 32 is a side elevational view of a cam lock bar used in the tibial section of the alignment jig assembly;

FIG. 33 is a plan view taken along the line 33—33 of FIG. 32;

FIG. 34 is a plan view of a cam used in a femoral section of the alignment jig assembly;

FIG. 35 is a plan view of a cam base plate used in the femoral section of the alignment jig assembly;

FIG. 36 is a view taken along the line 36—36 of FIG. 35;

FIG. 37 is a plan view of a cam adjustment slide used in the femoral section of the alignment jig assembly;

FIG. 38 is a view taken along the line 38—38 of FIG. 37;

FIG. 39 is a view taken along the line 39—39 of FIG. 37;

FIG. 40 is a plan view of a mounting and cam adjustment slide used in the femoral section of the alignment jig assembly;

FIG. 41 is a view taken along the line 41—41 of FIG. 40; and

FIG. 42 is a view taken along the line 42—42 of FIG. 40.

DESCRIPTION OF ONE SPECIFIC PREFERRED EMBODIMENT OF THE INVENTION

General Description

Figure 1:
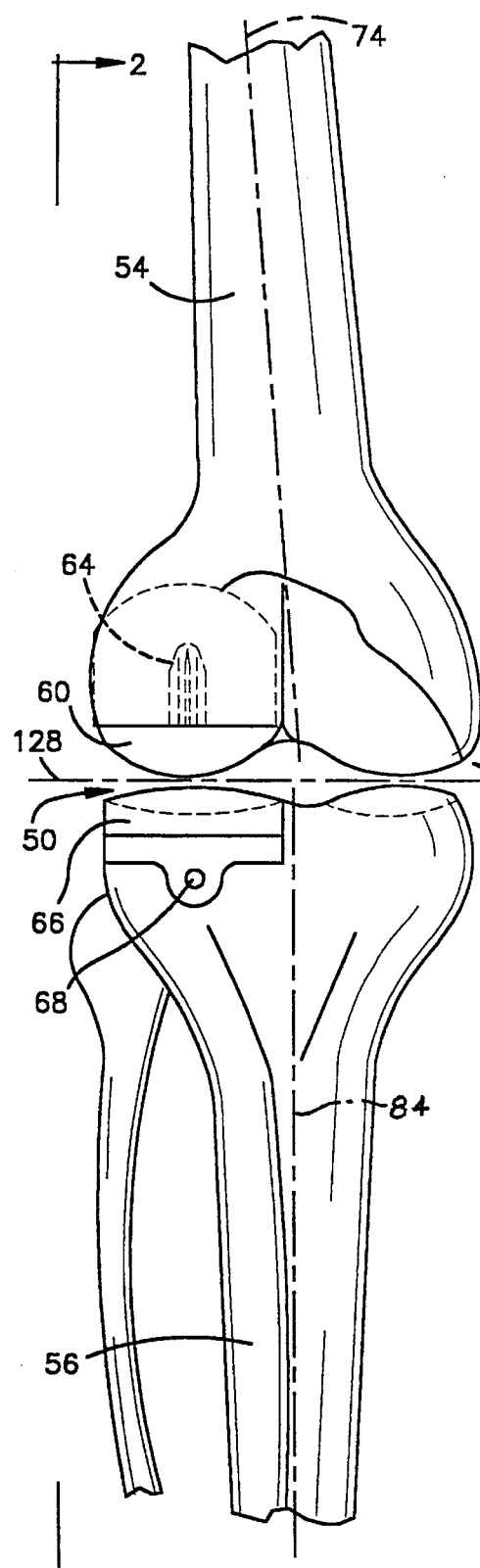
FIG. 1 is an anterior view illustrating the relationship of a femur and tibia with a unicompartmental knee replacement.
Figure 2:
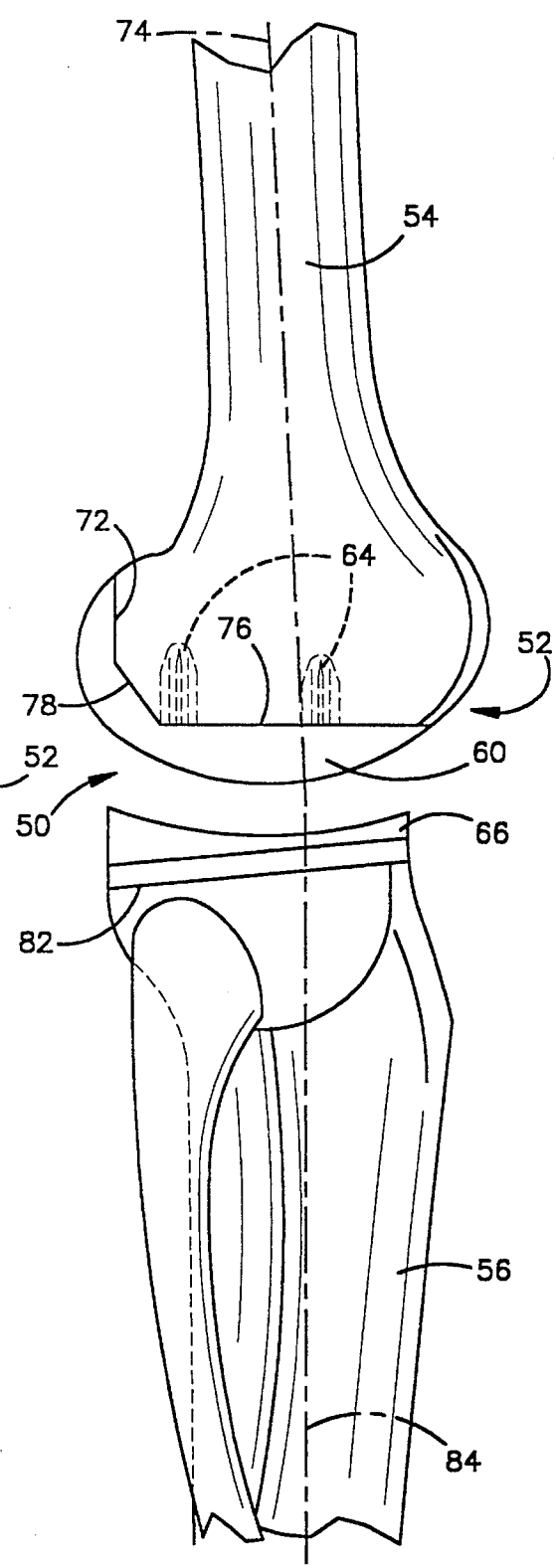
FIG. 2 is a lateral elevational view, taken along the line 2—2 of FIG. 1, further illustrating the unicompartmental knee replacement.

Although the method and apparatus of the present invention can be used in association with many different types of surgical procedures on many different parts of the body, the method and apparatus will be described in association with a unicompartmental knee replacement 50 (FIGS. 1 and 2). The unicompartmental knee replacement 50 is utilized in a knee joint 52 interconnecting a femur 54 and tibia 56. The unicompartmental knee replacement 50 is installed by arthroscopic surgery during the performance of arthroplasty on the knee joint 52.

The unicompartmental knee replacement 50 includes a femoral component 60 which is mounted on the femur 54 without screw fixation. This is accomplished by the use of intramedullary posts 64 having a cruciform shape. In addition, a tibial component 66 is mounted on the tibia 56 by a simple post or bicortical type screw 68.

In order to mount the femoral component 60 on the femur 54, three cuts are made during arthroscopic surgery to form mounting planes. Thus, a first cut is made to form a first mounting plane 72 (FIG. 2) on the femur 54. The first mounting plane 72 extends parallel to a longitudinal central axis 74 of the femur 54. A second cut is made to form a second mounting plane 76 on the femur 54. The second mounting plane 76 extends perpendicular to the axis 74 and to the mounting plane 72. A third cut is made to form a third mounting plane 78 on the femur 54. The third mounting plane 78 interconnects the planes 72 and 76 and is skewed at an angle of 45° to the axis 74 of the femur and the other two mounting planes 72 and 76.

Although the femoral component 60 has been illustrated herein as being connected with the femur 54 along three mounting planes 72, 76 and 78 formed on the femur 54, it should be understood that a greater or lesser number of planes could be used if desired, depending upon the design of the femoral component 60. In addition, it should be understood that although the planes 72, 76 and 78 have been illustrated as being at particular angles relative to each other and to the central axis 74 of the femur 54, the planes could be at different angles if desired.

The tibial component 66 is mounted on a single flat plane 82 formed by a single cut into the tibia 56. The flat plane 82 (FIG. 2) is skewed at an angle of between 3° and 5° relative to a longitudinal central axis 84 of the tibia 56. In addition to the post or bicortical type screw 68 (FIG. 1), bone growth promoting cement may be used to attach the tibial component 66 to the tibia 56. Of course, a greater number of mounting planes could be provided on the tibia 56 if desired. It should also be understood that although only a unicompartmental knee replacement 50 has been shown in FIGS. 1 and 2, it is contemplated that the method and apparatus of the present invention could be utilized with other surgical procedures, for example, with a full knee replacement.

Figure 5:
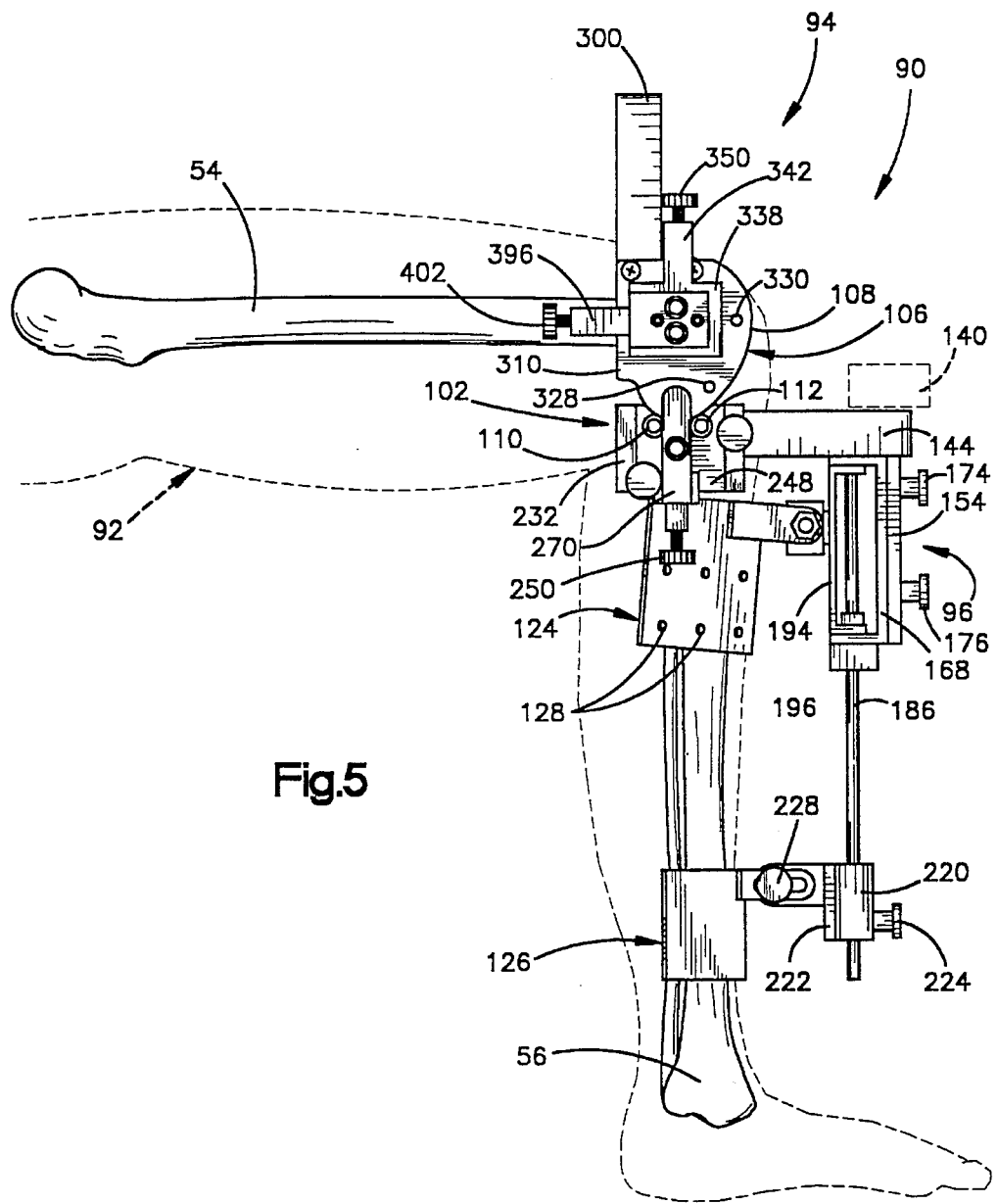
FIG. 5 is a side view illustrating the alignment jig assembly of FIGS. 3 and 4 on a leg with the leg flexed to a 90° position.
Figure 6:
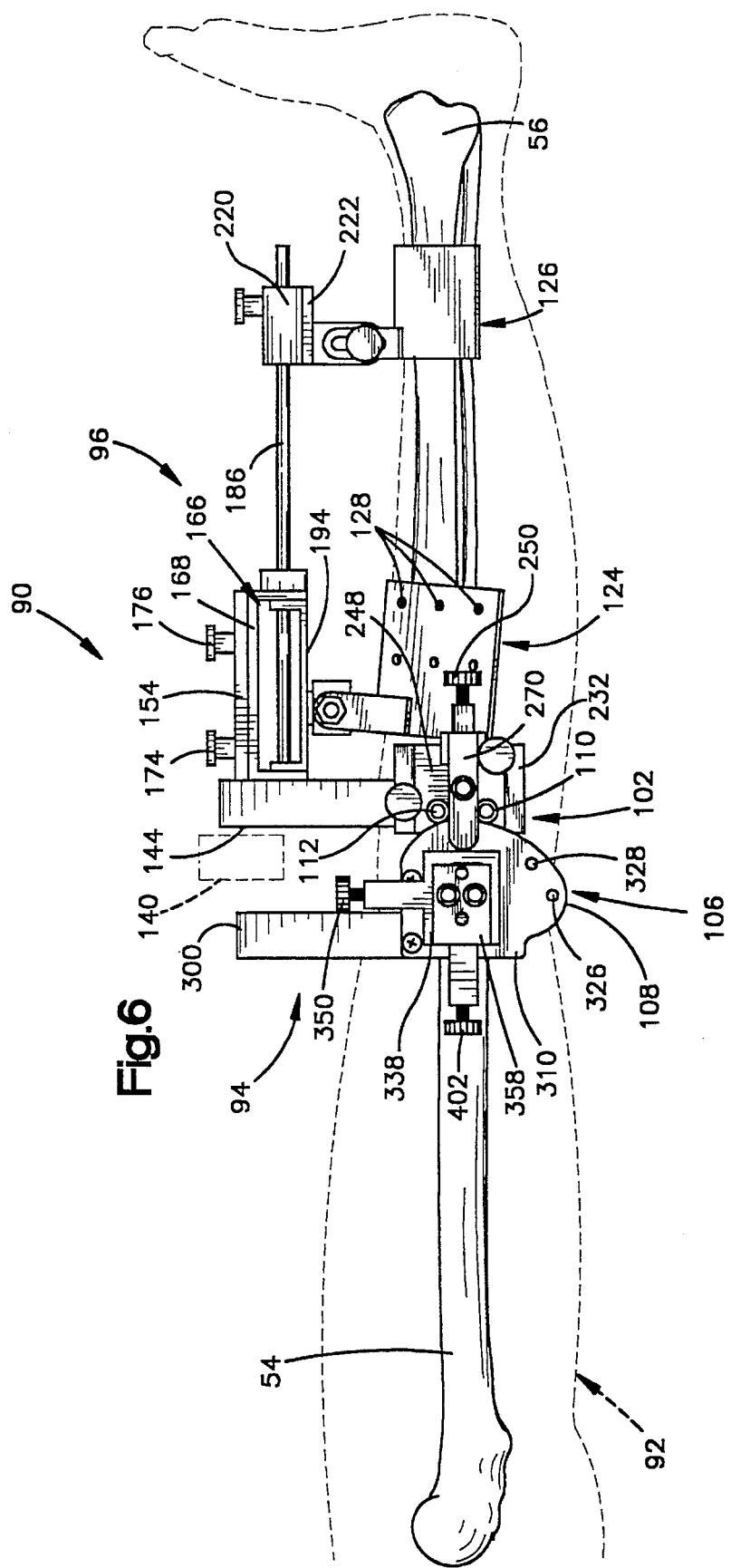
FIG. 6 is a side view illustrating the relationship of the alignment jig assembly to the leg when the leg is in an extended position.
Figure 7:
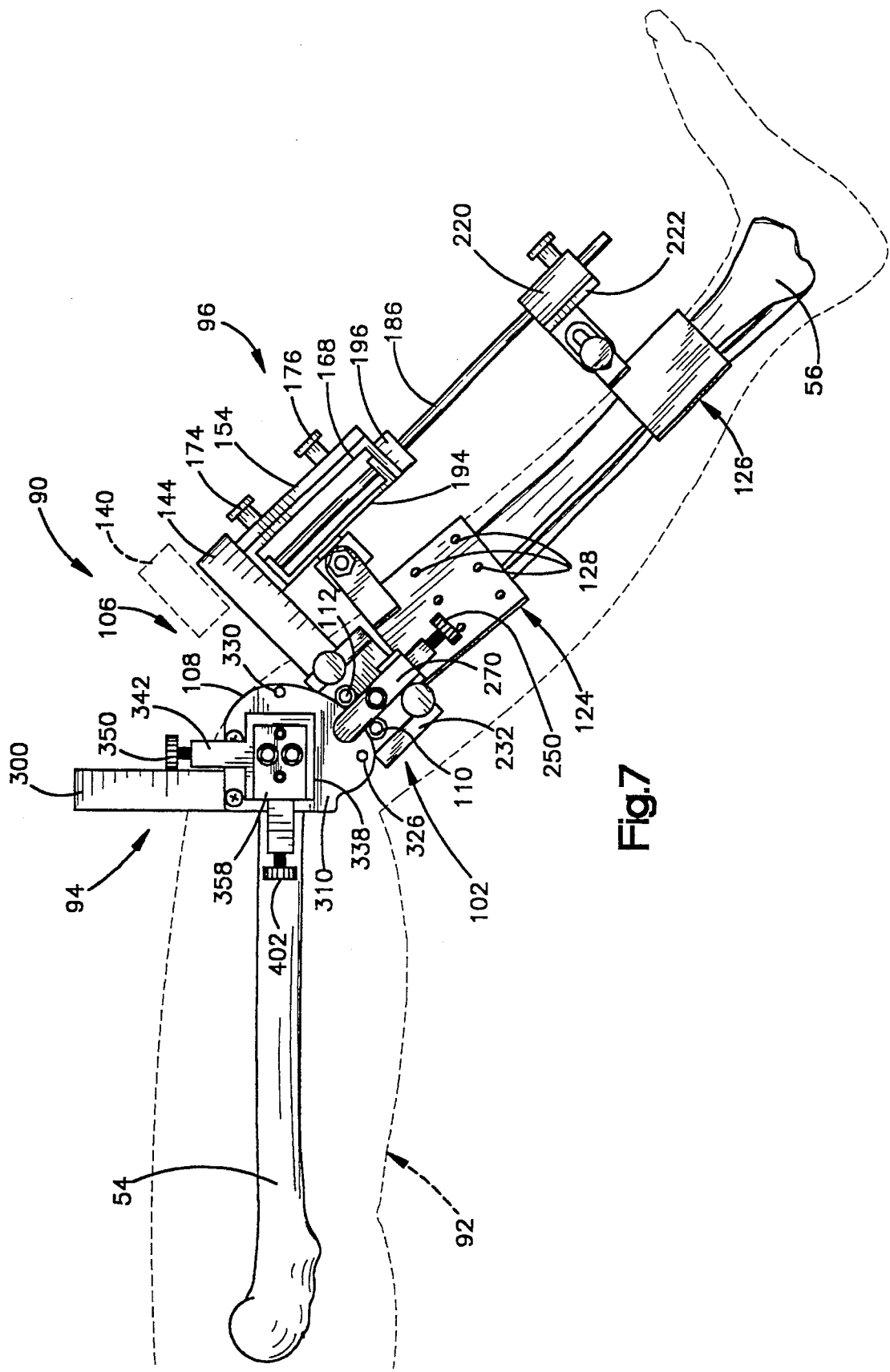
FIG. 7 is a side view illustrating the relationship of the alignment assembly jig to the leg when the leg is flexed to a 45° position.

An alignment jig assembly 90 (FIGS. 3 and 4) is constructed and utilized in accordance with the present invention. The alignment jig assembly 90 is utilized to position the femur 54 and tibia 56 of a leg 92 (FIGS. 5, 6 and 7) relative to each other during surgery. The alignment jig assembly 90 includes a femoral section 94 (FIGS. 3 and 4) and a tibial section 96. The femoral section 94 is fixedly secured with the femur 54 (FIGS. 5, 6 and 7). The tibial section 96 is fixedly connected with the tibia 56.

In accordance with one of the features of the invention, the separate femoral and tibial sections 94 and 96 can be securely interconnected in any one of a plurality of predetermined orientations relative to each other by an index assembly 102. This enables the femoral and tibial sections 94 and 96 of the alignment jig assembly 90 to retain the femur 54 and tibia 56 in any one of a plurality of predetermined orientations relative to each other during surgery. Since the index assembly 102 enables the femoral and tibial sections 94 and 96 to be repeatedly interconnected in any one of a plurality of predetermined positions, reproducible results which will be consistent from surgeon to surgeon can be obtained during operations. In addition, the series of cuts which form the mounting planes 72, 76, 78 and 82 (FIG. 2) on the femur 54 and tibia 56 will be accurately oriented at predetermined angles relative to each other and to the central axes 74 and 84 of the femur 54 and tibia 56.

Figure 4:
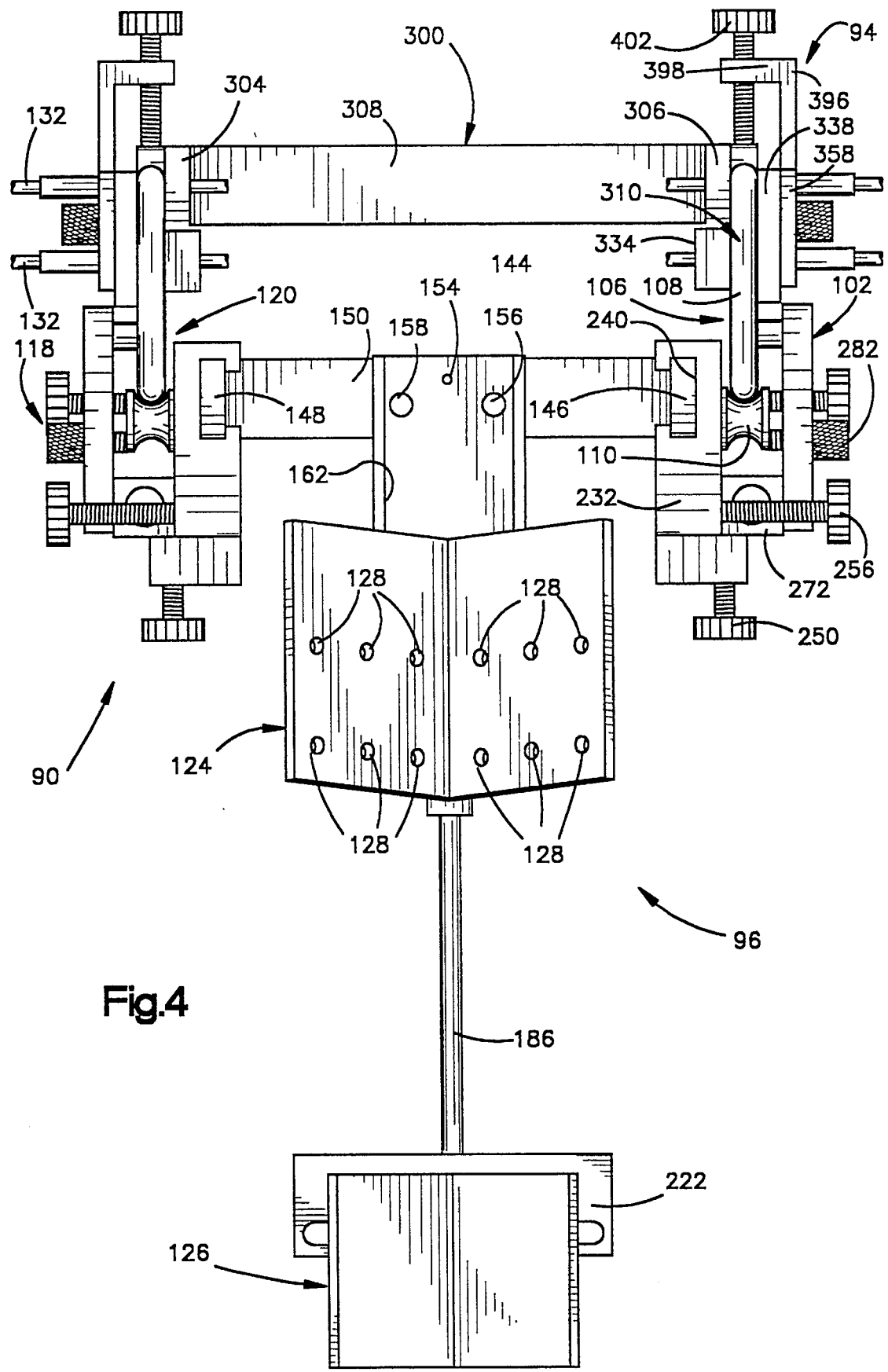
FIG. 4 is a rear elevational view, taken generally along the line 4—4 of FIG. 3, further illustrating the construction of the alignment jig assembly.

In accordance with one of the features of the invention, the femoral section 94 and tibial section 96 of the alignment jig assembly 90 are also interrelated by a positioning and support system 106 (FIGS. 3 and 4). The positioning and support system 106 includes a cam surface 108 which engages cam followers 110 and 112 (FIG. 3). The cam surface 108 and followers 110 and 112 cooperate to support and position the femur and tibia 54 and 56 during flexion or extension of the leg 92 (FIGS. 5, 6 and 7).

In accordance with another feature of the invention, the cam surface 108 and followers 110 and 112 can be utilized to effect distraction of the knee joint 52 which connects the femur 54 and tibia 56. Thus, the cam surface 108 and/or rollers 110 and 112 can be adjusted relative to each other to move end surfaces of the femur 54 and tibia 56 away from each other without injury or dislocation of parts of the knee joint. The cam surface 108 and the cam followers 110 and 112 cooperate to maintain the extent of distraction of the knee joint constant during flexion or extension of the leg 92 during surgery.

Although only a single index assembly 102 and positioning and support system 106 have been shown in FIG. 3, it should be understood that a second index assembly 118 and positioning and support system 120 is associated with the opposite side, that is the left (as viewed in FIG. 4) side of the alignment jig assembly. The left index assembly 118 (FIG. 4) has the same construction as the right index assembly 102. The two index assemblies 102 and 118 cooperate to retain the femoral and tibial sections 94 and 96 of the alignment jig assembly 90 in any one of the plurality of predetermined orientations relative to each other.

The left positioning and support system 120 (FIG. 4) has the same construction as the right positioning and support system 106. The two positioning and support systems 106 and 120 cooperate to support and position the femur 54 and tibia 56 during bending of the leg 92. In addition, the positioning and support systems 106 and 120 cooperate to effect distraction of the knee joint and to maintain the extent of distraction constant during bending of the leg 92.

Since the two positioning and support systems 106 and 120 are associated with opposite sides of the alignment jig assembly 90, opposite sides of the knee joint may be distracted to different extents. Thus, the lateral side of the knee joint may be distracted to a greater extent than the medial side of the knee joint by operating the one of the positioning and support systems 106 or 120 adjacent to the lateral side of the knee joint to a greater extent than the other positioning and support system. Even though the opposite sides of the knee joint may be distracted to different extents by the positioning and support systems 106 and 120, the positioning and support systems cooperate to maintain the amount of distraction on each side of the knee joint constant during flexion or extension of the leg.

The alignment jig assembly 90 may be used during the performance of surgical procedures which include distraction of the knee joint without the formation of mounting planes on the femur and/or tibia. The alignment jig assembly may be used to effect distraction of joints other than a knee joint. Of course, the size of the alignment jig assembly would be reduced if the alignment jig assembly is to be used during surgery on an ankle, finger or toe.

Mounting and Use of the Alignment Jig Assembly

When knee joint surgery is to be performed using the alignment jig assembly 90, the femoral and tibial sections 94 and 96 of the alignment jig assembly are first fixedly secured to the femur 54 and tibia 56 for movement therewith. It is preferred to mount the tibial section 96 on the tibia 56 before the femoral section 94 is mounted on the femur 54. Mounting of the tibial section 96 on the tibia 56 is preferably accomplished with the tibial section separate from the femoral section 94. If desired, the femoral section 94 could be mounted before the tibial section 96.

To mount the tibial section 96 on the tibia 56, the tibial section is first visually aligned with the tibial portion of the extended leg 92 (FIG. 6). To facilitate alignment of the tibial section 96 with the longitudinal central axis 84 of the tibia 56, a V-shaped locating and mounting bracket 124 is manually positioned against the outside of the tibial portion of the leg. The V-shaped configuration of the tibial locating and mounting bracket 124 enables the bracket to engage the tibial portion of the leg 92 and center itself relative to the leg. In addition, a V-shaped ankle bracket 126 is positioned in engagement with the outside of the tibial portion of the leg 92 adjacent to the ankle (FIG. 6). The V-shaped configuration of the ankle bracket 126 enables it to cooperate with the tibial portion of the leg adjacent to the ankle to further align the tibial section 96 with the longitudinal central axis 84 of the tibia 56.

Once the tibial section 96 has been aligned with the tibial portion of the leg 92, the tibial section is fixedly secured to the tibia 56. This is accomplished by a plurality of bone screws which are installed through openings 128 (FIGS. 3 and 4) in the tibial locating and mounting bracket 124. The bone screws extend into opposite sides of the tibia 56 (FIG. 6) at a plurality of locations along the longitudinal axis 84 of the tibia. By having the bone screws engage opposite sides of the tibia 56 at a plurality of locations along the longitudinal axis of the tibia, the tibial locating and mounting bracket 124 is fixedly secured to the tibia and held against movement along and/or transverse to the tibia.

Once the tibial locating and mounting bracket 124 has been fixedly secured to the tibia, the ankle bracket 126 is secured to the tibial portion of the leg by suitable means. Two preferred devices for securing the ankle bracket 126 to the leg are a Velcro® strap, preferably a stretchable Velcro® strap, and an inflatable cuff of the type used with a sphygmomanometer.

After the tibial section 96 has been fixedly secured to the tibia 56, the cam followers 110 and 112 in the positioning and support system 106 are accurately positioned relative to the transverse axis of the knee. To do this, the transverse axis 128 of the knee is first located using known techniques. The cam followers 110 and 112 are then moved relative to the tibial mounting section 96 to position the cam followers on opposite sides of and equal distances from a plane containing the longitudinal central axis 84 of the tibia 56 and the transverse axis 128 of the knee. The cam followers in the left (as viewed in FIG. 4) positioning and support system 120 are also moved to positions on opposite sides of and equal distances from the plane containing the longitudinal axis 84 of the tibia 56 and transverse axis 128 of the knee.

The femoral section 94 is then visually positioned on the femoral portion of the leg 92. At this time, the cam surface 108 in the positioning and support system 106 is midway within a range of adjustment relative to the femoral section 94. The femoral section 94 of the alignment jig assembly 90 is separate from and freely movable relative to the tibial section 96 of the alignment jig assembly prior to mounting of the femoral section on the leg 92.

As the femoral section 94 is visually positioned on the femoral portion of the leg 92, the cam surface 108 in the positioning and support system 106 is manually moved into abutting engagement with the cam follower rollers 110 and 112 connected with the tibial section 96. The cam surface on the cam in the left (as viewed in FIG. 4) positioning and support system 120 is manually moved into abutting engagement with the cam follower rollers connected with the left side of the tibial section 96. At this time, the femoral section 94 is visually aligned with the longitudinal central axis 74 of the femur 54. The index assemblies 102 and 118 may then be engaged to facilitate holding the femoral section 94 in position relative to the tibial section 96.

Once this has been done, a plurality of posts or shafts 132 (FIG. 4) are screwed into the femur 74 at a plurality of locations along the longitudinal axis 54 of the femur. Thus, two of the posts 132 are screwed into the lateral side of the femur 54 at spaced apart locations along the femur. Directly opposite from these posts are a separate pair of posts 132 which are screwed into the medial side of the femur at a pair of spaced apart locations along the femur. The posts 132 fixedly connect the femoral section 94 of the alignment jig assembly 90 with the femur 54 and hold the femoral section against movement along and transversely to the longitudinal central axis of the femur. Once this has been done, the femoral and tibial sections 94 and 96 of the alignment jig assembly 90 are interconnected by the patient's leg 92 (FIGS. 5, 6 and 7).

The position of the cam surface 108 in the positioning and support system 106 is adjustable along orthogonal axes. The position of the cam surface in the positioning and support system 120 is also adjustable along orthogonal axes. The adjustment axes for the cam surfaces in the positioning and support systems 106 and 120 are disposed in parallel planes which extend perpendicular to the transverse axis 128 of the knee 52 (FIG. 1). Once the cam surfaces (FIGS. 3 and 4) have been accurately positioned, they are secured against movement relative to the femoral section 94.

The cam surface 108 and the corresponding cam surface in the positioning and support system 120 have configurations which are a function of the relative movement which occurs between the femur and tibia during flexion of the leg.

Thus, the cam surface 108 has a configuration which corresponds to the configuration of the inferior end portion of the femur 54. The similarity between the configuration of the cam surface 108 and the configuration of the inferior end portion of the femur 54 can be seen by a comparison of the shape of the cam surface 108 in FIG. 3 with the shape of the inferior end portion of the femur 54 and component 60 in FIG. 2. The femoral component 60 cooperates with the femur 54 to obtain a configuration which corresponds to the configuration of the inferior end portion of a normal femur.

Once the cam surfaces in the positioning and support systems 106 and 120 have been located relative to each other and secured against movement relative to the femoral section 94, the cam surfaces remain in engagement with the associated cam followers during flexion or extension of the leg. Thus, the cam surface 108 (FIGS. 3 and 4) remains in engagement with the cam followers 110 and 112 throughout the range of movement of the leg 92. This enables the cams and followers in the positioning and support systems 106 and 120 to cooperate with the femoral section 94 and the tibial section 96 to support and position the femur 54 and the tibia 56 throughout the range of bending of the leg 92.

If the knee 52 of the leg 92 is to be distracted during surgery, the cam follower rollers 110 and 112 are moved relative to the tibia 56 in the superior direction, that is, upwardly as viewed in FIGS. 3 and 5 or toward the left as viewed in FIG. 6. This results in force being applied against the cam surface 108 to move the superior end of the tibia 56 away from the inferior end of the femur 54 without injury or dislocation of the components of the knee joint 52. Although only the cam surface 108 and followers 110 and 112 in the positioning and support system 106 are shown in FIGS. 3, 5 and 6, it should be understood that the cam surface and followers in the positioning and support system 120 on the opposite side of the alignment jig assembly 90 are also positioned to effect the desired distraction of the knee. Although it is preferred to effect distraction of the knee joint 52 by moving the cam followers in the positioning and support systems 106 and 120, distraction could be effected by moving the cams if desired.

Distraction of the knee 52 opens the joint to increase accessibility during surgery. In addition, the distraction facilitates correcting joint and/or ligament malfunctions. Therefore, it is believed that the alignment jig assembly 90 may be used during many different types of surgical procedures on knees or other joints.

The extent of lateral and medial distraction of the knee joint 52 may be the same or different depending upon the particular knee and the surgeon's desires. Thus, the positioning and support systems 106 and 120 can be actuated to distract opposite sides of the knee 52 to the same or different extents. Once the positioning and support systems 106 and 120 have been actuated to effect distraction of medial and lateral sides of the knee 52 to either the same or different extents, the extent of distraction of both the lateral and medial sides of the knee remains constant during flexion or extension of the leg 92 throughout its range of movement. This is because the cam surfaces in the positioning and support systems 106 and 120 have configurations which are functions of the relative movement between the femur and tibia of a normal leg during bending of the leg.

Once the femoral and tibial sections 94 and 96 have been mounted on the leg 92, a cutting tool 140 (FIGS. 5, 6 and 7) is mounted on the tibial section 96. The cutting tool 140 may be a drill, burr, mill, saw, or any other desired tool. However, a burr is presently preferred. A template type stop (not shown) is used to limit posterior movement of the cutting tool 140. This prevents accidental damage to the neurosurgical structures of the knee. It is contemplated that other devices may be mounted on the femoral and/or tibial sections 94 and 96 to facilitate surgery.

During a unicompartmental knee replacement operation, it is preferred to make the initial cut on the knee when the leg has been flexed to the 90° position shown in FIG. 5. By making the initial cut with the knee flexed to the 90° position of FIG. 5, exposure of the neurovascular structures to the cutting tool 140 is minimized during the making of the initial cuts. It is contemplated that suitable templates will be used as stops to limit movement of the cutting tool 140 during the making of all cuts on the knee. During the making of the initial cuts, there is minimal space in the knee joint and flexing of the leg to the 90° position (FIG. 5) prior to making the initial cuts is believed to be particularly advantageous.

During the making of an initial cut, the index assemblies 102 and 118 on opposite sides of the knee are engaged. The engaged index assemblies 102 and 118 hold the femoral section 94 and tibial section 96 of the alignment jig assembly 90 against movement relative to each other. In addition, the engaged index assemblies 102 and 118 accurately position the femoral and tibial sections 94 and 96 in an orientation in which the femur 54 and tibia 56 extend at the desired 90° angle relative to each other.

In performing a unicompartmental knee replacement operation, it is believed that it will be preferred to make the cut which forms the mounting plane 82 (FIG. 2) on the tibia 56 first. The cut is made by the cutting tool 140, indicated schematically in dashed lines in FIG. 5. As was previously mentioned, it may be preferred to make the tibial cut at an angle 3° to 5° relative to a plane extending perpendicular to the longitudinal central axis 84 of the tibia 56. Therefore, a 3° to 5° wedge may be used in association with the tool 140 to angle the tool. The wedge causes the tool 140 to form the downwardly and leftwardly (as viewed in FIG. 2) sloping mounting plane 82 which is skewed at an angle of 3° to 5° to a plane extending perpendicular to the central axis 84 of the tibia 56. Once the tibial cut has been made to form the mounting plane 82, the wedge is removed and the cutting tool 140 used to cut along an axis which extends perpendicular to the central axis 84 of the tibia.

Once the tibial mounting plane 82 has been formed and the wedge removed from the cutting tool 140, the cutting tool is advanced to cut the femur 54 to form the mounting plane 72. Since the leg 92 is held in the 90° of flexion position shown in FIG. 5 by the alignment jig assembly 90, the orientation of the mounting plane 72 will be parallel to the longitudinal axis 74 of the femur 54 and be skewed by 3° to 5° relative to the mounting plane 82 cut in the tibia 56.

Once the initial cuts have been made to form the mounting plane 82 on the tibia and the mounting plane 72 on the femur, the index assemblies 102 and 118 are released. This enables the leg to be extended from the 90° position of FIG. 5 to the fully extended or 0° position of FIG. 6. The cutting tool 140 remains on the tibial section 96 during bending of the leg 92. This results in the position of the cutting tool 140 relative to the tibia 56 remaining constant as the leg 92 is bent to thereby accurately position the cutting tool for the subsequent formation of the mounting planes 76 and 78.

During extension of the leg from the position shown in FIG. 5 to the position shown in FIG. 6, the cams in the positioning and support systems 106 and 120 are maintained in continuous engagement with their associated cam followers to guide and at least partially support the tibia 56 and/or femur 54. Due to the configuration of the cam surfaces, the femur 54 and tibia 56 move relative to each other with motions which correspond to their normal motions during bending of the leg 92 from the position shown in FIG. 5 to the position shown in FIG. 6, even though cuts have been made in both the femur 54 and tibia 56. During bending movement of the leg 92, the cams and followers in the positioning and support systems 106 and 120 cooperate to maintain the original amount of distraction of the knee 52 even though cuts have been made in both the femur 54 and tibia 56.

When the leg has been moved to the extended or 0° position of FIG. 6, the index assemblies 102 and 118 are again engaged. This locks the femoral and tibial sections 94 and 96 of the alignment jig assembly 90 against movement relative to each other, thus also blocking movement of the tibia 56 and femur 54 relative to each other. The second cut is then made on the femur 54 to form the mounting plane 76. During the making of the second cut, the femur 54 and tibia 56 are accurately positioned relative to each other by the cooperation between the index assemblies 102 and 118 and the femoral and tibial mounting sections 94 and 96. Therefore, the cutting tool 140 is accurately positioned relative to the femur 54 by the tibial section 96.

The second cut is made by moving the cutting tool 140 in a direction perpendicular to the longitudinal central axis 74 of the femur 54 and the mounting plane 72. Since the engaged index assemblies 102 and 118 hold the femoral and tibial sections 94 and 96 against relative movement, the femur 54 and tibia 56 are accurately positioned relative to each other and to the cutting tool 140 during the making of the cut which forms the mounting plane 72 and the making of the cut which forms the mounting plane 76. Therefore, the two mounting planes 72 and 76 are accurately positioned relative to each other at an angle which is the same as the angle through which the femoral and tibial sections 94 and 96 move relative to each other between making the cuts to form the mounting planes, that is, 90°.

The index assemblies 102 and 118 are then released. The leg 92 is then flexed through 45° of movement from the 0° or extended position shown in FIG. 6 to the position shown in FIG. 7. The index assemblies 102 and 118 are then re-engaged to lock the femoral and tibial sections 94 and 96 of the alignment jig assembly 90 in position. A cut is then made to form the mounting plane 78 on the femur 54.

The mounting plane 78 extends at an angle of 45° to both the mounting planes 72 and 76. During the forming of the cuts 72, 76 and 78 on the femur 54, the cuts were sequentially made with the planes 72, 76 and 78 extending perpendicular to the longitudinal central axis 84 of the tibia. This is because the cutting tool 140 is mounted on the tibial section 96 of the alignment jig assembly 90 and moves with the tibia 56 during flexion or extension of the leg 92. After the various cuts have been completed on the femur 54 and tibia 56, the unicompartmental knee components 60 and 66 are installed on the femur 54 and tibia 56.

Although the foregoing description has referred to unicompartmental knee replacement, it is contemplated that the alignment jig assembly 90 could be used during the performance of other surgical procedures. For example, the alignment jig assembly 90 could be used during a full knee replacement. It is also contemplated that the alignment jig assembly 90 will prove advantageous in operations which require distraction of the knee with or without cutting of the femur 54 and tibia 56. Alignment jig assemblies which have the same general construction and mode of operation as the alignment jig assembly 91 may be used during the surgery on joints other than knee joints.

The required number of cuts and mounting planes may vary from operation to operation. The angular relationship between the mounting planes may vary from operation to operation. In addition, the size of one patient's knee will probably be different from the size of another patient's knee. To accommodate different numbers of cuts and mounting planes, index assemblies 102 and 118 having different numbers of index locations will be used. To accommodate different angular relationships between mounting planes, index assemblies 102 and 118 having different index locations will be used. To accommodate knees of various sizes, cam surfaces 108 of various sizes will be used.

Alignment Jig Assembly—Tibial Section

The tibial section 96 of the alignment jig assembly 90 includes a generally U-shaped saddle or bracket 144 (FIGS. 3, 4, 8 and 9). The cutting tool 140 is mounted on the tibial saddle 144 (FIGS. 5, 6 and 7). Other devices may be mounted on the tibial saddle 144 along with the cutting tool 140. The tibial saddle 144 has a pair of arms 146 and 148 (FIG. 4) which are interconnected by a bight or cross section 150. A tibial slide 154 (FIGS. 3, 10 and 11) is fixedly secured at openings 156 and 158 (FIG. 10) and at corresponding openings 160 and 161 (FIGS. 8 and 9) on the inside of the cross section 150 of the tibial saddle 144.

The tibial slide 154 has a rectangular slot or recess 162 (FIGS. 10 and 11) in which a mounting bracket 166 (FIGS. 3, 12, 13, and 14) is received. The mounting bracket 166 has a rectangular base 168 from which arms 170 and 172 extend (FIGS. 12 and 13). A pair of lock screws 174 and 176 (FIG. 3) are connected with the base 168 and extend through slots 178 and 180 (FIG. 10) in the tibial slide 154. When the lock screws 174 and 176 (FIG. 3) are released, the mounting bracket 168 can be moved longitudinally along the slot 162 in the tibial slide 154.

A cylindrical rod 186 (FIGS. 3 and 4) extends through openings 188 and 190 (FIGS. 12 and 13) formed in the mounting bracket 166. A swivel plate 194 (FIGS. 3, 15, 16 and 17) is mounted on and pinned to the rod 186. The pin connection between the rod 186 and swivel plate 194 holds the rod against axial movement relative to the swivel plate. A clamp 196 (FIG. 3) grips the rod 186 and is secured to the mounting bracket 166. The clamp 196 holds the rod 186 against rotation relative to the mounting bracket 166. The swivel plate 194 has a cylindrical shank 200 (FIGS. 15–17) which extends outwardly from a base 202 of the swivel plate.

A bolt 203 (FIG. 3) extends through an opening 204 (FIG. 15) formed in the shank 200. A split clamp 214 (FIGS. 18 and 19) is disposed about the shank 200. The bolt 203 also extends through openings 206 and 208 formed in opposite halves 210 and 212 of the split clamp 214 (FIGS. 18 and 19). When the bolt 203 is loosened, the split clamp 214 can be rotated through a limited arcuate distance relative to the shank 200 of the swivel plate 194. When the bolt 203 is tightened, the clamp 214 frictionally grips the shank 200 of the swivel plate 194 and does not rotate relative to the swivel plate.

The tibial locating and mounting bracket 124 (FIGS. 3, 20 and 21) is connected with the swivel plate 194 by the bolt 203. When the bolt 203 is loosened, the tibial locating and mounting bracket 124 is free to pivot about the central axis of the bolt 203 and about the central axis of the shank 200. This enables the tibial locating and mounting bracket 124 to move into alignment with the tibial portion of the leg 92.

An ankle bracket mounting sleeve 220 (FIG. 3) is also mounted on the rod 186. An ankle bracket slide 222 is slidably connected with the mounting sleeve 200. A lock screw 224 can be tightened to lock the ankle bracket slide 220 against movement along the rod 186 and to hold the ankle bracket slide 222 against sliding movement relative to the sleeve. The ankle bracket 126 (FIGS. 3, 4, 22 and 23) is connected with the ankle bracket slide 222 by a lock screw 228 (FIG. 3). The ankle bracket 126 is movable relative to the ankle bracket slide 222 when the lock screw 228 is released. In addition, the ankle bracket slide 222 is movable relative to the sleeve when the lock screw 224 is released. Therefore, the position of the ankle bracket 126 can be adjusted to engage the tibial portion of the leg adjacent to the ankle.

A portion of the index assembly 102 and a portion of the positioning and support system 106 are mounted on the leg 146 (FIG. 3) of the tibial saddle 144. The index assembly 102 and the positioning and support system 106 can both be adjusted along two perpendicular axes relative to the tibial saddle 144. Thus, the portions of the index assembly 102 and support system 106 mounted on the tibial saddle 144 are adjustable along the central axis of the saddle arm 146 and are adjustable along an axis extending perpendicular to the central axis of the saddle arm. The two axes along which the index assembly 102 and positioning and support system 106 can be adjusted are parallel to a plane which extends perpendicular to the transverse axis 128 of the knee joint 52. These two degrees of freedom of adjustment of the portions of the index assembly 102 and positioning and support system 106 on the tibial saddle 144 enable them to be accurately positioned relative to a knee after the tibial section 96 has been fixedly connected with the tibia 56.

Figure 4A:
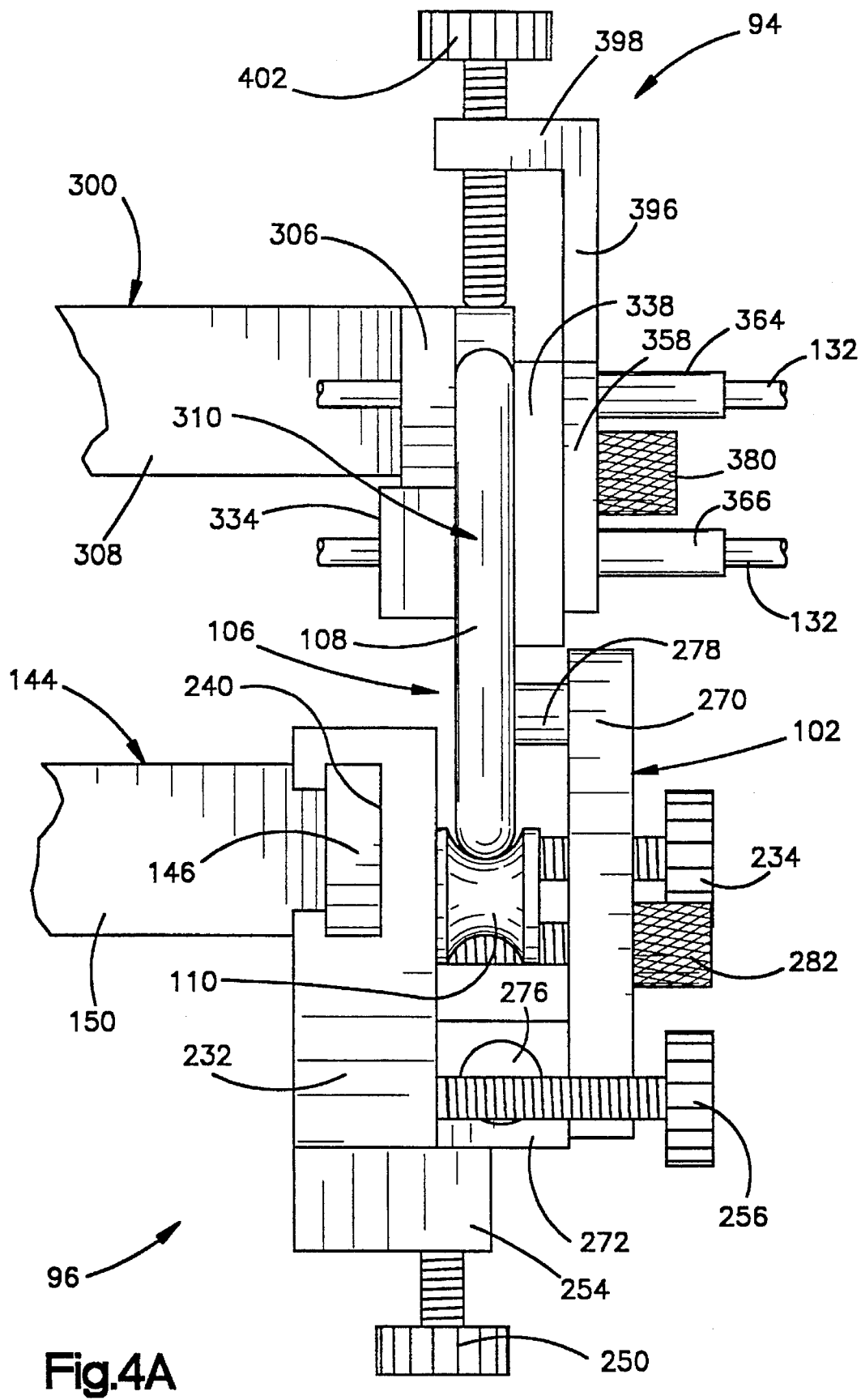
FIG. 4A is an enlarged view of a portion of the apparatus shown in FIG. 4.

A cam follower adjustment block 232 (FIGS. 3, 4A, 24, 25 and 26) is slidably mounted on the arm 146 of the tibial saddle 144. The cam follower adjustment block 232 has a through slot 240 (FIG. 24) in which the arm 146 of the tibial saddle 144 is received (FIG. 4A). A lock screw 234 (FIGS. 3 and 4A) is received in a threaded opening 236 (FIG. 25) formed in the cam follower adjustment block 232. Upon tightening of the lock screw 234, the cam followers 110 and 112 and the portion of the index assembly 102 on the tibial section 96 are held against movement along the arm 146 of the tibial saddle 144.

In addition, the cam follower adjustment block 232 has a cross slot 244 (FIGS. 25 and 26) which extends perpendicular to the slot 240. A cam follower guide block 48 (FIGS. 3, 27, 28 and 29) is slidably received in the cross slot 244 in the cam follower adjustment block 232. A positioning screw 250 (FIG. 3) extends through a threaded opening 252 (FIG. 24) formed in a projection 254 on the cam follower adjustment block 232 (FIGS. 24, 25 and 26).

Upon rotation of the positioning screw 250, the cam follower guide block 248 is moved along the cross slot 240 in the cam follower adjustment block 232. A lock screw 256 (FIGS. 3 and 4) is received in a threaded opening 260 (FIG. 27) in the cam follower guide block 248. Upon tightening of the lock screw 256, the cam follower guide block 248 is held against movement relative to the cam follower adjustment block 232.

The two perpendicular slots 240 and 244 (FIGS. 24, 25 and 26) in the cam follower adjustment block 232 enable the cam guide block 248 (FIGS. 27, 28 and 29) to be moved along either one of two perpendicular axes relative to the tibial saddle 144 and femoral section 94 (FIG. 3). Thus, the cam follower guide block 248 is movable in a direction perpendicular to the saddle arm 146 upon rotation of the adjustment screw 250. The cam follower guide block 248 and cam follower adjustment block 232 are movable together along the saddle arm 146 upon loosening of the block screw 234. The two degrees of freedom of movement of the cam follower guide block 248 enable it to be accurately positioned relative to the transverse axis 128 (FIG. 1) of the knee and the central axis 84 of the tibia.

A pair of openings 262 and 264 (FIG. 27) are provided in the cam follower guide block 248 to receive mounting screws for the identical cam followers 110 and 112. The cam follower 110 (FIGS. 30 and 31) has a circular configuration with an annular rim portion which is engaged by cam surface 108 (FIG. 3). An annular groove is formed in the rim of the cam follower 110 to receive the cam surface 108 and hold it against sideways movement.

The positions of the cam followers 110 and 112 can be adjusted along each of two axes relative to the cam surface 108. This is accomplished by moving the cam adjustment block 232 (FIGS. 3 and 4A) along the arm 146 of the tibial saddle 144 and by moving the cam follower guide block 248 in the slot 244 in the cam adjustment block 232 (FIGS. 25 and 26). The two axes along which the cam followers 110 and 112 can be adjusted are disposed in a plane which extends perpendicular to the transverse axis 128 of the knee 52 and parallel to the central axis 84 of the tibia 56.

The index assembly 102 includes a cam lock bar 270 (FIGS. 3, 4A, 32, and 33) which is pivotally mounted on the cam follower guide block 248. Thus, the cam follower guide block 248 includes a pair of upstanding ears or flanges 272 and 274 (FIGS. 27, 28 and 29). A hinge pin 276 (FIG. 4A) extends through an opening 276 (FIGS. 32 and 33) in the cam lock bar and is received in openings in the flanges 272 and 274 (FIG. 27 and 28) on the cam follower guide block 248.

The cam lock bar 270 has a projecting index pin 278 (FIG. 32) which is received in an opening at any one of a plurality of index locations connected with the femoral section 94. A lock screw 282 (FIG. 3) extends through the cam lock bar 270 into engagement with an opening 284 (FIG. 27) formed in the cam follower guide block 248. The lock screw 282 can be tightened to hold the lock bar 270 in an engaged position with the index pin 278 in engagement with an index location connected with the femoral section 94 of the alignment jig assembly 90. The lock screw 282 can be loosened to enable the lock bar 270 to pivot to a disengaged position in which the index pin 278 is disengaged from the index locations connected with the femoral section 94.

The lock bar 270 is mounted on the cam follower guide block 248. Therefore, the position of the lock bar 270 relative to the cam followers 110 and 112 remains constant during adjustment of the cam follower positions. Since the position of the lock bar 270 and index pin 278 is adjusted with the cam followers 110 and 112, the positions of the lock bar and index pin can also be adjusted along two perpendicular axes which are disposed in a plane extending perpendicular to the transverse axis 128 of the knee 52.

Although only the right (as viewed in FIG. 4) side of the tibial section 96 of the alignment jig assembly 90 has been illustrated in FIG. 3, it should be understood that the left (as viewed in FIG. 4) side of the tibial section 96 has the same construction as the right side. The components of the left side (as viewed in FIG. 4) of the tibial section 96 are the same as the components of the right side, that is, the same as is illustrated in FIGS. 8–32.

Alignment Jig Assembly—Femoral Section

The femoral section 94 (FIGS. 3 and 4) of the alignment jig assembly 90 is connected with the tibial section 96 by the index assembly 102. When the index assembly 102 is released, the femoral section 94 of the alignment jig assembly 90 can be separated from the tibial section 96 of the alignment jig assembly to facilitate mounting of the tibial section on the leg 92 of a patient. Of course, when the femoral section 94 and tibial section 96 of the alignment jig assembly 90 are both mounted on the leg 92 of a patient, they are interconnected by the leg of the patient.

The femoral section 94 of the alignment jig assembly 90 includes a generally U-shaped femoral saddle 300 (FIGS. 3 and 4). It is contemplated that cutting tools and/or other devices may be mounted on the femoral saddle 300. However, cutting tools or other devices on the femoral saddle 300 do not move relative to the femur 54 during bending of the leg as do cutting tools or other devices on the tibial saddle 144.

The femoral saddle 300 has the same general configuration as the tibial saddle 144. Thus, the femoral saddle 300 includes a pair of arms 304 and 306 (FIG. 4) which are interconnected by a base section 308. The femoral saddle 300 differs from the tibial saddle 144 in that downwardly (as viewed in FIGS. 3 and 4) extending end portions are formed on the arms 304 and 306. Thus, the arms 304 and 306 have a generally L-shaped configuration.

A cam 310 (FIGS. 3, 4, 4A, and 34) is fixedly secured to the end of the femoral saddle arm 306 by fasteners 312 (FIG. 3) which extend through openings 314 (FIG. 34) in the cam 310. A pair of generally rectangular openings 316 and 318 are formed in the central portion of the cam 310. In addition, a pair of adjustment slots 320 and 322 are formed in the cam.

A plurality of index locations 326, 328, and 330 (FIG. 34) are arranged in a noncircular arcuate array on the cam 310. The index locations 326, 238 and 330 form part of the index assembly 102 (FIG. 3). Thus, each of the index locations 326, 328, and 330 (FIG. 34) is engageable one-at-a-time by the index pin 278 (FIGS. 4A and 33) on the cam lock bar 270. The index locations 326, 328 and 330 are arranged in a noncircular arcuate array having the same configuration as the cam surface 108. Therefore, each index location 326, 328 or 330 is in the same spatial relationship relative to the followers 110 and 112, when that index location is engaged by the index pin 278.

When the leg 92 is flexed to the 90° position shown in FIG. 5, the index pin 278 (FIGS. 4A and 33) is engageable with the index location 326 (FIG. 34). When the leg 92 has been extended back to the 0° position of FIG. 6, the index pin 278 (FIGS. 4A and 33) is engageable with the index location 330 (FIG. 34). Similarly, when the knee is flexed to the 45° position shown in FIG. 7, the index pin 278 is engageable with the index location 328 (FIG. 34).

There is 45° of bending movement of the leg 92 between the position shown in FIG. 5 and the position shown in FIG. 7. There is also 45° of bending movement of the leg 92 between the position shown in FIG. 7 and the position shown in FIG. 6. Although there is the same extent of bending movement between positions of the leg 92 where the index pin 278 engages the openings 326 (FIG. 5), 328 (FIG. 7), and 330 (FIG. 6), the index openings 326,328 and 330 are spaced unequal distances apart. This is because of the combination sliding and pivoting movement which occurs in a knee when a leg is flexed or extended. Of course, the index openings could have a different spacing to correspond to different bending movements of the leg if desired.

In addition, either a greater or lesser number of index openings, corresponding to a greater or lesser number of leg positions, could be provided.

A cam base plate 334 (FIGS. 4A, 35 and 36) is mounted on the inside (toward the knee joint) of the cam 310. Threaded openings 336 and 338 (FIG. 35) in the cam base plate 334 are aligned with the adjustment slots 320 and 322 (FIG. 34) in the cam 310. Arcuate openings 340 and 342 (FIG. 35) in the cam base plate 334 cooperate with the cam adjustment openings 316 and 318 in the cam 310 (FIG. 34).

On the outside of the cam 310, opposite from the cam base plate 334, a cam adjustment slide 338 (FIGS. 3, 4A, 37, 38 and 39) is mounted. The cam adjustment slide 338 has a flat side 340 (FIGS. 38 and 39) which is positioned in flat abutting engagement with an outwardly facing major side surface of the cam 310 (FIGS. 3 and 4A). The cam adjustment slide 340 has an outwardly extending neck portion 342 (FIGS. 37 and 38) having a head end 344 (FIGS. 38 and 39) with a threaded opening 346 in which a positioning screw 350 (FIG. 3) is rotatably mounted. The positioning screw 350 abuts the cam 310 and is rotatable to move the cam 310 along a linear path or axis relative to the cam adjustment slide 338.

The cam adjustment slide 338 has a through slot 354 (FIGS. 37 and 38) in which a mounting and cam adjustment slide 358 (FIGS. 3, 4A, 40, 41 and 42) is mounted. The mounting and cam adjustment slide 358 has a generally rectangular base section 362 (FIGS. 40, 41 and 42) from which a pair of cylindrical tubular guide sections 364 and 366 extend. The guide sections 364 and 366 have a close tolerance sliding fit with the mounting posts 132 (FIG. 4). The mounting posts 132 are fixedly secured to the femur 54 and thus fix the mounting and cam adjustment slide 358 in position relative to the femur 56. The mounting and cam adjustment slide 358 functions as a base for the right (as viewed in FIG. 4) side of the femoral section 94.

The tubular guide sections 364 and 366 on the mounting and cam adjustment slide 358 extend through adjustment slots 370 and 372 (FIG. 37) formed in the cam adjustment slide 338 and through the openings 316 and 318 (FIG. 34) formed in the cam 310. The tubular guide sections 364 and 366 (FIGS. 40, 41 and 42) extend into the arcuate clearance openings 340 and 342 (FIG. 35) in the cam base plate 334. A pair of lock screws 380 and 382 (FIG. 3) extend through adjustment slots 384 and 386 (FIGS. 3 and 40) formed in the mounting and cam adjustment slide 358. The lock screws 380 and 382 extend through openings 388 and 390 (FIG. 37) formed in the cam adjustment slide 338. The lock screws 380 and 382 also extend through the adjustment slots 320 and 322 (FIG. 4) in the cam 310. The ends of the lock screws 380 and 382 (FIG. 3) are threaded into the openings 336 and 338 (FIG. 35) in the cam base plate 334.

When the lock screws 380 and 382 are tightened, the heads of the lock screws 380 and 382 bottom out on the outward ends of the guide sections 364 and 366. Continued rotation of the lock screws 380 and 382 thus draws the cam base plate 334 outwardly against the cam 310 and the cam base plate 334 applies pressure against the cam 310. The cam 310 presses against the side surface 340 (FIG. 38) of the cam adjustment slide 338 to firmly clamp the cam adjustment slide and cam 310 between the mounting and cam adjustment slide 358 (FIG. 40) and cam base plate 334 (FIG. 35). This clamping action holds the cam 310 in a desired position relative to the femoral section 94.

The mounting and cam adjustment slide 358 is provided with an outwardly extending neck portion 396 (FIGS. 40 and 41) having a head end 398 with a threaded opening 400 (FIG. 42) through which a positioning screw 402 (FIGS. 3 and 4A) is received. The positioning screw 402 abuttingly engages cam 310. Therefore, upon rotation of the positioning screw 402, the cam 310 moves relative to the mounting and cam adjustment slide 358.

The position of the cam 310 relative to the cam followers 110 and 112 (FIG. 3) can be adjusted along each of two perpendicular axes relative to the femur 54. The two axes lie in a plane which extends perpendicular to the transverse axis 128 of the knee. To enable the position of the cam 310 to be adjusted relative to the posts 132 (FIG. 4) and femur 54, the lock screws 380 and 382 are loosened somewhat to reduce the clamping force on the cam.

The positioning screw 350 can then be actuated to move the cam 310 along a horizontal (as viewed in FIG. 3) axis relative to the posts 132 and to the mounting and cam adjustment slide 358. The positioning screw 402 can be adjusted to move the cam 310 along a vertical (as viewed in FIG. 3) axis relative to the posts 132 and to the mounting and cam adjustment slide 358. The two degrees of freedom of movement of the cam 310 enable it to be accurately positioned relative to the transverse axis 128 (FIG. 1) of the knee and to the central axis 74 of the femur. The two perpendicular axes along which the cam 310 can be adjusted are disposed in a plane which extends perpendicular to the transverse axis 128 of the knee 52 and parallel to the central axis 74 of the femur 54.

Although only the cam 310 for the right (as viewed in FIG. 4) side of the femoral section 94 is shown in FIGS. 3 and 34, it should be understood that the left side (as viewed in FIG. 4) of the femoral section 94 has the same construction as the right side. Thus, each side of the femoral section 94 contains a set of the components illustrated in FIGS. 34–42.

After the tibial section 96 has been mounted on the tibial portion of the leg 92, the cam follower rollers 110 and 112 are positioned relative to the transverse axis 128 of the knee. After the transverse axis 128 (FIG. 1) of the knee 52 has been located, the lock screw 234 (FIG. 3) is loosened and the cam follower adjustment block 232 is moved along the tibial saddle arm 146. When the cam followers 110 and 112 are disposed on opposite sides of and evenly spaced from the transverse axis 128 of the knee 52, the lock screw 234 is tightened to hold the cam follower adjustment block 232 against movement relative to the tibial saddle arm 146.

The lock screw 256 (FIG. 3) is then loosened. The cam follower guide block 248 is then moved relative to the cam follower adjustment block 232 by rotating the positioning screw 250. When the cam followers 110 and 112 are a predetermined distance from the transverse axis 128 (FIG. 1), the lock screw 256 (FIG. 3) is again tightened to hold the cam follower guide block 248 against movement relative to the cam follower adjustment block 232. The distance which the cam followers 110 and 112 are positioned from the transverse axis 128 of the knee 52 is a function of the physical characteristics of the knee and/or the surgery to be performed.

The femoral section 94 is mounted on the femoral portion of the extended leg 92 (FIG. 6). This is done with the cam 310 and cam adjustment slide 338 in the centers of their ranges of adjustment relative to the mounting and cam adjustment slide 358 and posts 132. At this time, the locking screws 380 and 382 have been tightened to hold the components of the femoral mounting section 94 against movement relative to each other.

The cams on opposite sides of the femoral mounting section 94 are then positioned in engagement with the cam followers on opposite sides of the tibial mounting section 96. Thus, the cam surface 108 on the cam 310 is positioned in engagement with the cam followers 110 and 112. The femoral mounting section is then visually aligned with the femoral portion of the extended leg 92.

The femoral section 94 is then mounted on the femur 54 by engaging the femur with the mounting posts 132 (FIG. 4) in the manner previously described. The tubular guide sections 364 and 366 on the mounting and cam adjustment slide 358 (FIGS. 40, 41 and 42) position the mounting posts 132 parallel to each other and facilitate locating the mounting posts perpendicular to the longitudinal central axis 74 of the femur 54. Although it is believed that it will be preferred to have the index assemblies 102 and 118 engaged to interconnect the femoral section 94 and tibial section 96 during mounting of the femoral section 94, the index assemblies may be disengaged if desired.

Once the femoral section 94 has been connected with the femur 54 by the mounting posts 132 (FIG. 4), the index assemblies 102 and 118 are disengaged to enable the leg 92 to be bent and the femoral and tibial sections 94 and 96 to move relative to each other. In addition, the retaining screws 380 and 382 are loosened somewhat to enable the cam 310 and cam adjustment slide 338 to move relative to the mounting and cam adjustment slide 358.

The leg 92 is then flexed from the 0° position shown in FIG. 6 to the 90° position shown in FIG. 5. The positioning screws 350 and 402 are then operated to position the cam 310 in engagement with the cam followers 110 and 112. Force can also be manually applied to the cam 310 to aid in positioning the cam. The retaining screws 380 and 382 are then lightly tightened to provide a frictional grip between the mounting and cam adjustment slide 358, the cam adjustment slide 338, the cam 310 and the cam base plate 334.

The leg 92 is then extended from the 90° position of FIG. 5 to the 0° position of FIG. 6. As this occurs, the cam surface 108 on the cam 310 will tend to remain in engagement with the followers 110 and 112. This is because the cam surface 108 has a configuration which is a function of the relative movement between the femur 54 and tibia 56. However, manual pressure may be applied against the cam 310 to ensure that the cam surface 108 remains in engagement with the followers 110 and 112 as the leg 92 is bent from the 90° position of FIG. 5 to the extended or 0° position of FIG. 6.

Once the leg 92 has been moved to the extended or 0° position of FIG. 6, the retaining screws 380 and 382 are further tightened to securely clamp the cam 310 and cam adjustment slide 338 between the cam base plate 334 and the mounting and cam adjustment slide 358. Once the retaining screws 380 and 382 have been tightened, the leg 92 is again bent through its range of movement to be certain that the cam surface 108 remains in engagement with the cam followers 110 and 112 throughout the range of movement of the leg. If for some unforeseen reason the cam surface 108 does not remain in engagement with the cam followers 110 and 112, the retaining screws 380 and 382 are loosened and the position of the cam 310 adjusted so that the cam surface 108 remains in engagement with the cam followers 110 and 112 throughout the range of bending movement of the leg 92.

Although the foregoing description of the adjustment of the cam 310 relates only to the apparatus on the right (as viewed to FIG. 4) side of the alignment jig assembly 90, the apparatus on the left side of the jig assembly 90 is adjusted in the same manner and at the same time as the apparatus on the right side of the alignment jig assembly. Thus, the cams on the medial and lateral sides of the leg 92 are adjusted to remain in contact with the cam follower rollers on the medial and lateral sides of the leg.

Once the position of the cam 310 has been adjusted so that the cam surface 108 remains in engagement with the cam followers 110 and 112 throughout the range of bending movement of the leg 92, the knee joint may be distracted if desired. To distract the knee joint, the lock screw 256 is loosened and the positioning screw 250 (FIG. 3) is rotated to move the cam follower guide block 248 (FIGS. 3, 27, 28 and 29) upwardly (as viewed in FIG. 3) relative to the cam follower adjustment block 232 (FIGS. 3, 24, 25 and 26). This applies force against the cam surface 108.

The force between the cam followers 110 and 112 and cam 310 is transmitted through the femoral and tibial sections 94 and 96 to the femur 54 and tibia 56. This force pulls the side of the knee joint adjacent to the cam 310 and cam followers 110 and 112 apart to distract the side of the knee joint adjacent to the right (as viewed in FIG. 4) portion of the femoral section 94. The apparatus on the left (as viewed in FIG. 4) portion of the alignment jig assembly 90 can also be adjusted in the same manner as the apparatus on the right to distract the side of the knee joint adjacent to the left (as viewed in FIG. 4) side of the alignment jig assembly 90. Since the right and left sides of the alignment jig assembly 90 are adjusted separately, the amount of distraction of one side of the knee joint can be different than the amount of distraction of the opposite side of the knee joint if desired.

Since the cam surface 108 in the apparatus adjacent to the right side of the knee and the corresponding cam surface in the apparatus adjacent to the left side of the knee have configurations which are a function of the relative movement between the femur and tibia during bending movement of the leg 92, the amount of distraction of the knee remains constant during bending movement of the leg. Thus, if the alignment jig assembly 90 has been adjusted to distract the lateral and medial sides of the knee to equal extents, the amount of the distraction of the lateral and medial sides of the knee joint remains equal and constant during bending movement of the knee joint. Similarly, if the alignment jig assembly 90 has been adjusted to distract the lateral side of the knee joint to a greater extent than the medial side, the amount of distraction of the lateral and medial sides remains constant during bending movement of the joint with the lateral side distracted to a greater extent than the medial side.

It is preferred to distract the knee joint 52 by moving the cam followers 110 and 112 toward the cam 310. However, if desired, the knee joint 52 could be distracted by moving the cam 310 toward the cam followers 110 and 112. When this is to be done, the positioning screw 402 (FIGS. 3 and 4A) is rotated to move the cam 310 and femoral saddle 300 downwardly (as viewed in FIGS. 3 and 4A) relative to the mounting and cam adjustment slide 358.

It should be noted that it is often necessary to position a retractor, a light, a scope, a cutting device, or another instrument relative to the knee joint during surgery. In accordance with a feature of the invention, the tibial saddle 144 may also be used to support any such device in addition to the cutting tool 140. Additionally, the tibial saddle 144 may be used to mount a device like the selectively rigidifiable instrument support arm shown in U.S. Pat. No. 3,858,578. Such a device can be used to selectively position a surgical device of this kind relative to the knee joint and then fix it in position. Since the alignment jig assembly 90 is constantly fixed in proper position relative to the femoral and tibial parts of the knee joint, the supported device will properly move relative to the knee joint during movement of the knee or during the operation. Thus, it is seen that the invention provides a linked platform across a joint for the placement or holding of instruments during surgery.

Conclusion

The present invention provides a new and improved apparatus 90 and method for use in positioning the femur 54 and tibia 56 of a leg 92 relative to each other during surgery. The apparatus 90 and method are advantageously used during unicompartmental knee replacements. However, the apparatus 90 and method can be used during other surgical procedures on many different parts of the body.

The apparatus 90 includes a femoral section 94 which is connected with the femur 54 for movement therewith. A tibial section 96 is connected with the tibia 56 for movement therewith. The two sections 94 and 96 are movable relative to each other during flexion or extension of the leg 92.

An index assembly 102 is provided to retain the femoral and tibial sections 94 and 96 in any one of a plurality of predetermined orientations relative to each other during surgery. Since the femur 54 and tibia 56 can be held in any one of a plurality of predetermined orientations (FIGS. 5, 6 and 7) during surgery, there is reproducible alignment of the femur and tibia at each of the predetermined orientations to facilitate the making of accurate cuts during surgery. It is believed that this will avoid many of the problems which have been encountered using known unicompartmental knee replacement systems 50. However, it will also be useful during other surgical procedures.

The apparatus 90 includes a cam 310 which cooperates with the followers 110 and 112 to support and position the femur 54 and tibia 56 during flexion or extension of the leg. The cam 310 has a surface 308 with a configuration which is a function of the relative movement which naturally occurs between the femur 54 and tibia 56 during bending movement of the leg 92. Therefore, the cam 310 cooperates with the cam followers 110 and 112 to support and position the femur 54 and tibia 56 for natural movement relative to each other as the leg 92 is moved during surgery.

In addition, the cam 310 and followers 110 and 112 cooperate with each other to effect distraction of a knee joint interconnecting the femur 54 and tibia 56. Thus, the cam 310 and followers 110 and 112 can be adjusted to transmit force which separates the end portions of the femur 54 and tibia 56. The cam 310 and the followers 110 and 112 cooperate to maintain the extent of separation of the end portions of the femur 54 and tibia 56 constant during movement of the leg. The extent of distraction of the medial portion of the knee can be different than the extent of distraction of the lateral portion of the knee if desired. However, the extent of distraction of both portions of the knee is kept constant as the leg is moved. This enables the normal mechanical transverse axis 128 of the knee to be established during surgery.

It is contemplated that the apparatus and method of the invention will be used in conjunction with surgery on many different parts of the body. Thus, it is believed that the concepts relative to joint distraction may be used in conjunction with surgery on fingers, ankles or toes. It is also believed that the concepts relating to positioning of one part of a body relative to another may be used in conjunction with surgery on fingers, ankles, or toes.

We claim:

1. Apparatus for use in surgery on a leg having a femur and a tibia and a knee joint with a knee axis of rotation, said apparatus comprising:

a femoral portion and means for securing said femoral portion to the femur, said femoral portion being secured to the femur at a first location spaced from the knee axis of rotation;

a tibial portion and means for securing said tibial portion to the tibia;

connection means on said tibial portion and said femoral portion for electively connecting said tibial portion to said femoral portion for relative movement about an apparatus axis of rotation, said connection means being movable between (a) a locking condition fixing said tibial portion and said femoral portion in a selected one of a plurality of predetermined rotational positions within the range of motion of the knee joint and thus blocking movement of the knee joint and (b) a release condition allowing relative movement of said tibial and femoral portions and thus allowing movement of the knee joint through its range of motion, said connection means comprises means for fixing the distance between said first location and the knee axis of rotation at different values when corresponding to different ones of said plurality of predetermined rotational positions;

said means for securing said femoral portion to the femur comprising means for securing said femoral portion to the femur comprising means for securing said femoral portion to the femur at a location spaced from the apparatus axis of rotation; and a cam having a cam surface with a varying-radius profile on one of said femoral and tibial portions and a cam follower on the other one of said femoral and tibia portions, said cam follower being engageable with said cam surface during movement of the knee joint through its range of motion.

2. An apparatus as set forth in claim 1 further including a cam surface connected with one of said first and second sections and a follower connected with another of said first and second sections and engageable with said cam surface during flexion or extension of the leg, said cam surface having a configuration which is a function of the relative movement between the femur and tibia during flexion or extension of the leg.

3. An apparatus as set forth in claim 1 wherein said means for mounting said second section on the tibia includes means for fixedly securing the second section to the tibia at a mounting location, said second section and mounting location being movable relative to said first section along a longitudinal axis of the tibia during flexion or extension of the leg.

4. An apparatus as set forth in claim 1 wherein said index means includes adjustable means connected with one of said first and second sections for defining a plurality of index locations, said apparatus further including means for use in positioning said adjustable means relative to said one of said first and second sections to locate said plurality of index locations relative to said one of said first and second sections.

5. An apparatus as set forth in claim 4 wherein said means for positioning said adjustable means relative to said one of said first and second sections includes retainer means operable between a retaining condition holding said adjustable means against movement relative to said one of said first and second sections and a release condition enabling said adjustable means to move relative to said one of said first and second sections with at least two degrees of freedom of movement.

6. An apparatus as set forth in claim 4 wherein said adjustable means includes a cam surface and a follower, at least one of said cam surface and follower being adjustable relative to said one of said first and second sections.

7. An apparatus as set forth in claim 1 wherein said means for mounting said first section on the femur includes means for engaging a first side of the femur at a plurality of locations spaced apart in an axial direction along the first side of the femur and means for engaging a second side of the femur at a plurality of locations spaced apart in an axial direction along the second side of the femur, said means for mounting said second section on the tibia includes means for engaging a first side of the tibia at a plurality of locations spaced apart in an axial direction along a first side of the tibia and means for engaging a second side of the tibia at a plurality of locations spaced apart in an axial direction along the second side of the tibia.

8. An apparatus as set forth in claim 1 wherein said index means includes a plurality of index locations connected with one of said first and second sections and disposed in a noncircular arcuate array and means connected with the other of said first and second sections for engaging each of the index locations in turn.

9. An apparatus as set forth in claim 1 wherein said index means includes a first plurality of index locations disposed adjacent to a first side of the leg, each index location of said first plurality of index locations corresponding to a different orientation of the femur and tibia relative to each other, a second plurality of index locations disposed adjacent to a second side of the leg opposite from the first side of the leg, each index location of said second plurality of index locations corresponding to an orientation of the femur and tibia which is the same as an index location of the first plurality of index locations, first retainer means for engaging each of the index locations in the first plurality of index locations in turn, and second retainer means for engaging an index location in the second plurality of index locations which corresponds to an orientation of the femur and tibia which is the same as an index location engaged by said first retainer means.

10. An apparatus as set forth in claim 1 wherein said index means includes a plurality of spaced apart openings connected with one of said first and second sections and means for engaging each of said openings in turn connected with another of said first and second sections.

11. An apparatus as set forth in claim 1 further including means for effecting distraction of a knee joint interconnecting the femur and tibia, said means for effecting distraction including means for separating end portions of the femur and tibia and for maintaining the extent of separation of the end portions of the femur and tibia constant during flexion or extension of the leg.

12. An apparatus as set forth in claim 1 further including a first cam surface disposed adjacent to a first side of the leg, said first cam surface having a configuration which is a function of the configuration of at least a portion of an end portion of one of the femur and tibia, a second cam surface disposed adjacent to a second side of the leg opposite from the first side of the leg, said second cam surface having a configuration which is a function of the configuration of at least a portion of an end portion of one of the femur and tibia, a first cam follower disposed adjacent to the first side of the leg and engageable with the first cam surface during flexion or extension of the leg, and a second cam follower disposed adjacent to the second side of the leg and engageable with the second cam surface during flexion or extension of the leg.

13. An apparatus as set forth in claim 12 wherein said index means includes a first plurality of index locations connected with said first cam surface, each index location of said first plurality of index locations corresponding to a different orientation of the femur and tibia relative to each other, a second plurality of index locations connected with said second cam surface, each index location of said second plurality of index locations corresponding to an orientation of the femur and tibia which is the same as an index location of the first plurality of index locations, first retainer means for engaging each of the index locations in said first plurality of index locations to retain said first cam surface and said first cam follower against relative movement, and second retainer means for engaging an index location in said second plurality of index locations which corresponds to an index location engaged by said second retainer means to retain said second cam surface and second cam follower against relative movement.

14. An apparatus as set forth in claim 12 further including means for adjusting the position of said first and second cam surfaces relative to each other to effect distraction of one portion of a knee joint interconnecting the femur and tibia to a greater extent than another portion of the knee joint.

15. An apparatus as set forth in claim 12 further including means for adjusting the position of said first and second cam followers relative to each other to effect distraction of one portion of a knee joint interconnecting the femur and tibia to a greater extent than another portion of the knee joint.

16. An apparatus for use in positioning the femur and tibia of a leg relative to each other during surgery, said apparatus comprising a first section, means for connecting said first section with the femur, a second section, means for connecting said second section with the tibia, a first cam surface connected with a first one of said first and second sections and disposed adjacent to a first side of the leg, a second cam surface connected with the first one of said first and second sections and disposed adjacent to a second side of the leg, said first and second cam surfaces having configurations which are a function of the relative movement between the femur and tibia during flexion or extension of the leg, a first follower connected with a second one of said first and second sections, and a second follower connected with said second one of said first and second sections, said first follower being disposed in engagement with said first cam surface during flexion or extension of the leg and said second follower being disposed in engagement with said second cam surface during flexion or extension of the leg, said first follower and said first cam surface being movable relative to each other during flexion or extension of the leg, said second follower and said second cam surface being movable relative to each other during flexion or extension of the leg.

17. An apparatus as set forth in claim 16 further including first means for adjusting the position of at least one of said first cam surface and said first follower relative to said first and second sections and second means for adjusting the position of at least one of said second cam surface and said second follower relative to said first and second sections.

18. An apparatus as set forth in claim 16 further including first surface means connected with said first cam surface for defining a first plurality of openings, first retainer means connected with said first follower for engaging each of the openings in said first plurality of openings in turn, second surface means connected with said second cam surface for defining a second plurality of openings, and second retainer means connected with said second follower for engaging each of the openings in said second plurality of openings in turn.

19. An apparatus as set forth in claim 16 wherein said first one of said first and second sections includes a base, said apparatus further including means for enabling said first cam surface to move relative to said base along a first axis and along a second axis which extends perpendicular to said first axis, and means for enabling said second cam surface to move relative to said base along a third axis which extends parallel to the first axis and along a fourth axis which extends parallel to the second axis.

20. An apparatus as set forth in claim 19 wherein said second one of said first and second sections includes second base, said apparatus further including means for enabling said first follower to move relative to said second base along a fifth axis and along a sixth axis which extends perpendicular to the fifth axis, and means for enabling said second follower to move relative to said second base along a seventh axis which extends parallel to the fifth axis and along an eighth axis which extends parallel to the sixth axis.

21. An apparatus as set forth in claim 16 wherein said means for connecting said second section with the tibia includes a locating member having a generally V-shaped cross sectional configuration, said locating member cooperating with the tibia to center the locating member relative to the tibia.

22. An apparatus as set forth in claim 16 wherein said means for connecting said first section with the tibia includes a first connector member which engages the tibia, said means for connecting said second section with the femur including a second connector member which engages the femur, said first and second connector members being spaced apart by a first distance as measured along longitudinal axes of the femur and tibia when the leg is extended, said first and second connector members being spaced apart by a second distance which is greater than the first distance, as measured along the longitudinal axes of the femur and tibia when the leg is flexed at an angle of 90°.

23. An apparatus as set forth in claim 16 further including means for effecting distraction of a knee joint interconnecting the femur and tibia, said means for effecting distraction including means for changing the positions of said first and second followers relative to said second one of said first and second sections.

24. An apparatus as set forth in claim 16 wherein said means for connecting said first section with the femur includes means for mounting said first section on the femur, said means for connecting said second section with the tibia includes means for mounting said second section on the tibia.

25. An apparatus as set forth in claim 16 further including index means for retaining said first and second sections in any one of a plurality of predetermined orientations relative to each other to retain the femur and tibia in any one of a plurality of orientations relative to each other during surgery.

26. An apparatus for use in positioning the femur and tibia of a leg relative to each other during surgery, said apparatus comprising a first section, means for connecting said first section with the femur, a second section, means for connecting said second section with the tibia, first means for defining a first plurality of index locations disposed in a first noncircular arcuate array having a configuration which is a function of the relative movement between the femur and tibia during bending of the leg, said first means being disposed adjacent to a first side of the leg and being connected with a first one of said first and second sections, each index location of said first plurality of index locations corresponding to a different one of a plurality of predetermined orientations of the femur and tibia relative to each other, second means for defining a second plurality of index locations disposed in a second noncircular arcuate array having a configuration which is a function of the relative movement between the femur and tibia during bending of the leg, said second means being disposed adjacent to a second side of the leg and being connected with the first one of said first and second sections, each index location of said second plurality of index locations corresponding to a different one of the plurality of predetermined orientations of the femur and tibia relative to each other, first retainer means disposed adjacent to the first side of the leg for engaging each of the index locations in said first plurality of index locations in turn, said first retainer means being connected with a second one of said first and second sections, and second retainer means disposed adjacent to the second side of the leg for engaging an index location in said second plurality of index locations which corresponds to the same orientation of the femur and tibia as an index location engaged by said first retainer means, said first and second means and said first and second retainer means cooperating with said first and second sections to retain the femur and tibia in each of the predetermined orientations in turn.

27. An apparatus as set forth in claim 26 wherein said means for connecting said first section with the femur includes a plurality of members which engage the femur at a plurality of locations space apart along a longitudinal axis of the femur, said means for connecting said second section with the tibia including a plurality of members which engage the tibia at a plurality of locations spaced apart along a longitudinal axis of the tibia.

28. An apparatus as set forth in claim 27 wherein said first and second sections are movable relative to each other in such a manner as to vary a distance measured along the longitudinal axes of the femur and tibia and extending between said members which engage the femur and said members which engage the tibia during flexion or extension of the leg.

29. An apparatus as set forth in claim 26 wherein a distance between a transverse axis of a knee joint interconnecting femur and tibia and each index location of said first plurality of index locations is the same when each index location is engaged by said first retainer means and a distance between the transverse axis of the knee joint and each index location of said second plurality of index locations is the same when each index location is engaged by said second retainer means.

30. An apparatus as set forth in claim 26 further including means for adjusting the location of said first plurality of index locations relative to the first one of said first and second sections along a first axis and along a second axis which extends perpendicular to the first axis and means for adjusting the location of said second plurality of index locations relative to the first one of said first and second sections along a third axis and along a fourth axis which extends perpendicular to the third axis.

31. An apparatus as set forth in claim 26 wherein said means for connecting said first section with the femur includes means for mounting said first section on the femur for movement therewith, said means for connecting said second section with the tibia including means for mounting said second section on the tibia for movement therewith.

32. An apparatus as set forth in claim 26 wherein said first means for defining a first plurality of index locations includes means for defining a plurality of index locations which are spaced unequal distances apart in the first noncircular arcuate array, said second means for defining a second plurality of index locations includes means for defining a plurality of index locations which are spaced unequal distances apart in the second noncircular arcuate array.

33. An apparatus as set forth in claim 26 further including means for effecting distraction of a knee joint interconnecting the femur and tibia, said means for effecting distraction of the knee joint including means for moving end portions of the femur and tibia away from each other and for maintaining the extent of separation between end portions of the femur and tibia constant during flexion or extension of the leg.

34. An apparatus as set forth in claim 26 further including means for adjusting the positions of said first and second pluralities of index locations relative to each other to enable one portion of a knee joint interconnecting the femur and tibia to be distracted a greater extent than another portion of the knee joint.

35. An apparatus as set forth in claim 26 further including a first cam surface connected with the first one of said first and second sections in a fixed spatial relationship with said first plurality of index locations, a second cam surface connected with the first one of said first and second sections in a fixed spatial relationship with said second plurality of index locations, a first follower connected with the second one of said first and second sections, and a second follower connected with the second one of said first and second sections, said first follower being disposed in engagement with said first cam surface during flexion or extension of the leg and said second follower being disposed in engagement with said second cam surface during flexion or extension of the leg.

36. An apparatus as set forth in claim 35 wherein said first plurality of index locations, said first cam surface, said second plurality of index locations, and said second cam surface are all connected with said first section.

37. An apparatus for use in positioning the femur and tibia of a leg in a plurality of orientations relative to each other during surgery, said apparatus comprising a first section, means for connecting said first section with the femur, a second section, means for connecting said second section with the tibia, said first and second sections being movable relative to each other during flexion or extension of the leg to change the orientation of the femur and tibia relative to each other during surgery, and means for effecting distraction of a knee joint interconnecting the femur and tibia, said means for effecting distraction including means for moving end portions of the femur and tibia away from each other and for maintaining the extent of separation of end portions of the femur and tibia constant during flexion or extension of the leg to change the orientation of the femur and tibia relative to each other during surgery.

38. An apparatus as set forth in claim 37 wherein said means for moving end portions of the femur and tibia away from each other and maintaining the extent of separation of the end portions of the femur and tibia constant during flexion or extension of the leg includes means for moving medial and lateral portions of the end portions of the femur and tibia through different distances and for maintaining the extent of separation of the medial and lateral portions of the end portions of the femur and tibia constant during flexion or extension of the leg.

39. An apparatus as set forth in claim 37 wherein said means for moving end portions of the femur and tibia away from each other and for maintaining the extent of separation of the end portions of the femur and tibia constant during flexion or extension of the leg includes a first cam surface connected with a first one of the femur and tibia adjacent to a medial side of the knee joint, a second cam surface connected with said first one of the femur and tibia adjacent to a lateral side of the knee joint, a first cam follower connected with a second one of the femur and tibia adjacent to the medial side of the knee joint, and a second cam follower connected with said second one of the femur and tibia adjacent to the lateral side of the knee joint, said first cam surface and said first cam follower being disposed in engagement with each other throughout flexion or extension of the leg through at least a portion of its range of movement and said second cam surface and said second cam follower being disposed in engagement with each other throughout flexion or extension of the leg through at least a portion of its range of movement.

40. An apparatus as set forth in claim 39 wherein said first and second cam surfaces are adjustable relative to said first one of the femur and tibia and said first and second cam followers are adjustable relative to said second one of the femur and tibia to enable the medial and lateral portions of the femur and tibia to be moved away from each other through different distances.

41. An apparatus as set forth in claim 37 further including index means for retaining said first and second sections in any one of a plurality of predetermined orientations relative to each other to retain the femur and tibia in any one of a plurality of orientations relative to each other during surgery.

42. An apparatus as set forth in claim 37 wherein said means for moving end portions of the femur and tibia away from each other and for maintaining the extent of separation of the end portions of the femur and tibia constant during flexion or extension of the leg includes a cam surface connected with one of said first and second sections and a follower connected with the another of said first and second sections, said cam surface having a configuration which is a function of the relative movement between the femur and tibia during flexion or extension of the leg.

43. An apparatus as set forth in claim 37 wherein said means for connecting said first section with the femur includes means for connecting said first section with the femur at a plurality of locations which are spaced apart along a longitudinal axis of the femur, said means for connecting said second section with the tibia includes means for connecting said second section with the tibia at a plurality of locations which are spaced apart along a longitudinal axis of the femur, said means for moving end portions of the femur and tibia away from each other and for maintaining the extent of separation of the end portions of the femur and tibia constant during flexion or extension of the leg including means for enabling said second section to move relative to said first section along a longitudinal axis of the tibia during flexion or extension of the leg.

44. An apparatus as set forth in claim 37 further including a plurality of index locations connected with a first one of said first and second sections and disposed in a noncircular array and means connected with a second one of said first and second sections for engaging each of said index locations in turn to locate the femur and tibia relative to each other.

45. A method of positioning a femur and tibia of a leg relative to each other during surgery, said method comprising the steps of aligning a cam with a first one of the femur and tibia, fixedly connecting the cam with the first one of the femur and tibia, aligning a follower with a second one of the femur and tibia, fixedly connecting the follower with the second one of the femur and tibia, thereafter, bending the leg to change the position of the femur and tibia relative to each other, and maintaining the cam and follower in engagement during said step of bending the leg.

46. A method as set forth in claim 45 further including the step of maintaining the femur and tibia in a first position relative to each other by retaining the cam and follower against movement relative to each other prior to performance of said step of bending the leg, after performance of said step of maintaining the femur and tibia in the first position relative to each other, performing said step of bending the leg, thereafter, maintaining the femur and tibia in a second position relative to each other by retaining the cam and follower against movement relative to each other.

47. A method as set forth in claim 45 further including the step of distracting a knee interconnecting the femur and tibia prior to performance of said step of bending the leg, and maintaining the extent of distraction of the knee constant during said step of bending the leg.

48. A method as set forth in claim 47 wherein said step of distracting the knee includes separating medial and lateral portions of end portions of the femur and tibia to different extents, said step of maintaining the extent of distraction of the knee constant during said step of bending the leg includes maintaining the different extents of separation of the medial and lateral portions of the end portions of femur and tibia constant at the different extents of distraction.

49. A method as set forth in claim 45 further including the step of fixedly connecting a first mounting section with the first one of the femur and tibia at a plurality of locations along a longitudinal axis of the first one of the femur and tibia, said step of aligning a cam with the first one of the femur and tibia includes the step of fixedly securing the cam with the first mounting section after fixedly connecting the first mounting section with the first one of the femur and tibia, said method further including the step of fixedly connecting a second mounting section with the second one of the femur and tibia at a plurality of locations along a longitudinal axis of the second one of the femur and tibia, said step of aligning a follower with the second one of the femur and tibia includes the step of fixedly securing the follower with the second mounting section after fixedly connecting the second mounting section with the second one of the femur and tibia.

50. A method as set forth in claim 45 wherein said step of aligning a follower with a second one of the femur and tibia is performed prior to performance of said step of aligning a cam with a first one of the femur and tibia.

51. A method as set forth in claim 45 wherein said steps of aligning a cam with a first one of the femur and tibia and aligning a follower with a second one of the femur and tibia include locating a transverse axis of a knee interconnecting the femur and tibia, positioning the cam relative to the transverse axis of the knee, and positioning the follower relative to the transverse axis of the knee.

52. A method as set forth in claim 51 wherein said step of positioning the cam relative to the transverse axis of the knee includes moving the cam in a plane which extends generally perpendicular to the transverse axis of the knee, said step of positioning the follower relative to the transverse axis of the knee includes moving the follower in a plane which extends generally perpendicular to the transverse axis of the knee.

53. A method as set forth in claim 45 wherein said step of aligning the cam with a first one of the femur and tibia includes moving the leg and moving the cam relative to the first one of the femur and tibia during performance of said step of bending the leg.

54. A method as set forth in claim 45 further including the step of connecting a first mounting section with the first one of the femur and tibia at a plurality of locations along a longitudinal axis of the first one of the femur and tibia, and connecting a second mounting section with the second one of the femur and tibia at a plurality of locations along a longitudinal axis of the second one of the femur and tibia, said step of connecting a first mounting section with a first one of the femur and tibia being performed with the first mounting section spaced apart from the second mounting section and with the cam and follower spaced apart from each other.

55. A method as set forth in claim 54 wherein said steps of aligning the cam with the first one of the femur and tibia and aligning the follower with the second one of the femur and tibia includes moving the cam and follower into abutting engagement.

56. A method as set forth in claim 54 wherein said step of connecting the second mounting section with the second one of the femur and tibia includes engaging the tibial portion of the leg with a positioning member having a generally V-shaped cross sectional configuration to locate the second mounting section relative to the tibia.

57. A method as set forth in claim 54 wherein said step of connecting a first mounting section with the first one of the femur and tibia is performed with the cam disposed on the first mounting section, said steps of connecting a second mounting section with a second one of the femur and tibia is performed with the follower disposed on the second mounting section, said method further including the step of moving the cam and follower relative to the first and second mounting sections after performing said steps of connecting the first mounting section with the first one of the femur and tibia and connecting the second mounting section with the second one of the femur and tibia.

58. A method of positioning a femur and tibia of a leg relative to each other during surgery, said method comprising the steps of connecting a first mounting section with a first one of the femur and tibia at a plurality of locations along a longitudinal axis of the first one of the femur and tibia, connecting a second mounting section with a second one of the femur and tibia at a plurality of locations along a longitudinal axis of the second one of the femur and tibia, thereafter, bending the leg to a first predetermined position, said step of bending the leg to a first predetermined position including effecting relative movement between the first and second mounting sections, interconnecting the first and second sections to retain the leg in the first predetermined position, making a first cut on the femur while first and second mounting sections are interconnected with the leg in the first predetermined position, disconnecting the first and second mounting sections to release the leg for movement from the first predetermined position, thereafter bending the leg from the first predetermined position to a second predetermined position, said step of bending the leg to a second predetermined position including effecting relative movement between the first and second mounting sections, interconnecting the first and second mounting sections to retain the leg in the second predetermined position, and making a second cut on the femur while the first and second mounting sections are interconnected with the leg in the second predetermined position.

59. A method as set forth in claim 58 wherein said step of bending the leg from the first predetermined position to the second predetermined position includes bending the leg through a first angle, said step of making a first cut on the femur includes making the first cut with at least a portion of the first cut disposed in a first plane, said step of making a second cut including making the second cut with at least a portion of the second cut in a second plane which extends at the first angle relative to the first plane.

60. A method as set forth in claim 58 wherein said step of bending the leg from the first predetermined position to the second predetermined position includes varying a distance measured along the longitudinal axes of the femur and tibia and extending between the first and second sections.

61. A method as set forth in claim 58 further including the steps of distracting a knee joint interconnecting the femur and tibia and maintaining the extent of distraction of the knee joint constant during performance of said step of bending the leg from the first predetermined position to the second predetermined position.

62. A method as set forth in claim 58 further including the step of maintaining a cam connected with the first mounting section in engagement with a follower connected with the second mounting section during performance of said step of bending the leg from the first predetermined position to the second predetermined position.

63. A method as set forth in claim 58 wherein said step of connecting a first mounting section with a first one of the femur and tibia is performed with the second mounting section disconnected from the first mounting section.

64. A method of positioning a femur and tibia of a leg in a plurality of positions relative to each other during surgery, said method comprising the steps of distracting a knee joint interconnecting the femur and tibia, thereafter, bending the leg at the knee joint from a first position to a second position by causing flexion or extension of the leg about the knee joint, and maintaining the extent of distraction of the knee joint constant during bending of the leg at the knee joint with flexion or extension of the leg about the knee joint.

65. A method as set forth in claim 64 wherein said step of distracting the knee joint includes separating end portions of the femur and tibia, said step of maintaining the extent of distraction of the knee joint constant during bending of the knee joint including maintaining the separation of the end portions of the femur and tibia constant during bending of the leg.

66. A method as set forth in claim 64 wherein said step of distracting a knee joint includes separating the femur and tibia by a first distance at a first portion of the knee joint and separating the femur and tibia by a second distance at a second portion of the knee joint, said first distance being greater than said second distance, said step of maintaining the extent of distraction of the knee joint constant during bending of the knee joint includes maintaining the first and second distances constant during bending of the knee joint.

67. A method as set forth in claim 64 wherein said step of distracting a knee joint includes moving one of a cam and cam follower relative to one of the femur and tibia while maintaining the position of another one of the cam and cam follower constant relative to another one of the femur and tibia.

68. A method as set forth in claim 64 further including the steps of aligning a cam with a first one of the femur and tibia, and aligning a follower with a second one of the femur and tibia, said step of maintaining the extent of distraction of the knee joint constant during bending of the knee joint including transmitting force between a cam and cam follower during bending of the knee joint.

69. A method as set forth in claim 68 further including the step of maintaining the cam and cam follower in engagement during said step of bending the leg.

70. A method as set forth in claim 64 further including the steps of aligning a cam with a first one of the femur and tibia, and aligning a cam follower with a second one of the femur and tibia, said steps of aligning a cam with a first one of the femur and tibia and aligning a cam follower with a second one of the femur and tibia including moving one of the cam and cam follower relative to one of the femur and tibia while maintaining the position of another one of the cam and cam follower constant relative to another one of the femur and tibia.

71. A method as set forth in claim 64 further including the steps of positioning first and second cams adjacent to opposite sides of the knee, said step of positioning first and second cams adjacent to opposite sides of the knee including connecting a first mounting section with a first one of the femur and tibia, positioning first and second cam followers adjacent to opposite sides of the knee, said step of positioning first and second cam followers adjacent to opposite sides of the knee including connecting a second mounting section with a second one of the femur and tibia, said step of distracting the knee including transmitting force from the first and second cams to the first one of the femur and tibia through the first mounting section and transmitting force from the first and second cam followers to the second one of the femur and tibia through the second mounting section.

72. A method as set forth in claim 71 further including the step of maintaining the first cam and first cam follower in engagement during performance of said step of bending of the leg from the first position to the second position, and maintaining the second cam and second cam follower in engagement during bending of the leg from the first position to the second position.

73. A method of positioning a femur and tibia of a leg relative to each other during surgery, said method comprising the steps of aligning a cam with a first one of the femur and tibia, aligning a follower with a second one of the femur and tibia, thereafter, bending the leg to change the position of the femur and tibia relative to each other, maintaining the cam and follower in engagement during said step of bending the leg, fixedly connecting a first mounting section with the first one of the femur and tibia at a plurality of locations along a longitudinal axis of the first one of the femur and tibia, said step of aligning a cam with the first one of the femur and tibia includes the step of fixedly securing the cam with the first mounting section after fixedly connecting the first mounting section with the first one of the femur and tibia, said method further including the step of fixedly connecting a second mounting section with the second one of the femur and tibia at a plurality of locations along a longitudinal axis of the second one of the femur and tibia, said step of aligning a follower with the second one of the femur and tibia includes the step of fixedly securing the follower with the second mounting section after fixedly connecting the second mounting section with the second one of the femur and tibia, said step of bending the leg includes moving the first and second mounting sections relative to each other.

74. A method as set forth in claim 73 further including the step of maintaining the femur and tibia in a first position relative to each other by retaining the cam and follower against movement relative to each other prior to performance of said step of bending the leg, after performance of said step of maintaining the femur and tibia in the first position relative to each other, performing said step of bending the leg, thereafter, maintaining the femur and tibia in a second position relative to each other by retaining the cam and follower against movement relative to each other.

75. A method as set forth in claim 73 further including the step of distracting a knee interconnecting the femur and tibia prior to performance of said step of bending the leg, and maintaining the extent of distraction of the knee constant during said step of bending the leg.

76. A method as set forth in claim 75 wherein said step of distracting the knee includes separating medial and lateral portions of end portions of the femur and tibia to different extents, said step of maintaining the extent of distraction of the knee constant during said step of bending the leg includes maintaining the different extents of separation of the medial and lateral portions of the end portions of femur and tibia constant at the different extents of distraction.

77. A method as set forth in claim 73 wherein said step of aligning a follower with a second one of the femur and tibia is performed prior to performance of said step of aligning a cam with a first one of the femur and tibia.

78. A method as set forth in claim 73 wherein said steps of aligning a cam with a first one of the femur and tibia and aligning a follower with a second one of the femur and tibia include locating a transverse axis of a knee interconnecting the femur and tibia, positioning the cam relative to the transverse axis of the knee, and positioning the follower relative to the transverse axis of the knee.

79. A method as set forth in claim 78 wherein said step of positioning the cam relative to the transverse axis of the knee includes moving the cam in a plane which extends generally perpendicular to the transverse axis of the knee, said step of positioning the follower relative to the transverse axis of the knee includes moving the follower in a plane which extends generally perpendicular to the transverse axis of the knee.

80. A method as set forth in claim 73 wherein said step of aligning the cam with a first one of the femur and tibia includes moving the leg and moving the cam relative to the first one of the femur and tibia during performance of said step of bending the leg.

81. A method as set forth in claim 73 wherein said step of connecting a first mounting section with a first one of the femur and tibia being performed with the first mounting section spaced apart from the second mounting section and with the cam and follower spaced apart from each other.

82. A method as set forth in claim 81 wherein said steps of aligning the cam with the first one of the femur and tibia and aligning the follower with the second one of the femur and tibia includes moving the cam and follower into abutting engagement.

83. A method as set forth in claim 81 wherein said step of connecting the second mounting section with the second one of the femur and tibia includes engaging the tibial portion of the leg with a positioning member having a generally V-shaped cross sectional configuration to locate the second mounting section relative to the tibia.

84. A method as set forth in claim 73 wherein said step of connecting a first mounting section with the first one of the femur and tibia is performed with the cam disposed on the first mounting section, said step of connecting a second mounting section with a second one of the femur and tibia is performed with the follower disposed on the second mounting section, said method further including the step of moving the cam and follower relative to the first and second mounting sections after performing said steps of connecting the first mounting section with the first one of the femur and tibia and connecting the second mounting section with the second one of the femur and tibia.

85. A method as set forth in claim 73 further including the steps of positioning the femur and tibia in a first orientation relative to each other, making a first cut on the femur with at least a portion of the first cut in a first plane, bending the leg through a first angle to change the angular orientation of the femur and tibia and to position the femur and tibia in a second orientation relative to each other, thereafter, making a second cut on the femur with at least a portion of the second cut in a second plane which extends at the first angle relative to the first plane, bending the leg through a second angle to change the angular orientation of the femur and tibia and to position the femur and tibia in a third orientation relative to each other, and, thereafter, making a third cut on the femur with at least a portion of the third cut in a third plane which extends at the second angle relative to the second plane.

86. Apparatus as defined in claim 1 wherein said means for securing said tibial portion to the tibia comprises means for securing said tibial portion to the tibia at a location spaced from the apparatus axis of rotation.

87. A method of positioning a femur and tibia of a leg relative to each other during surgery, said method comprising the steps of aligning a cam with a first one of the femur and tibia, aligning a follower with a second one of the femur and tibia, thereafter, positioning the femur and tibia in a first orientation relative to each other, making a first cut on the femur with at least a portion of the first cut in a first plane, bending the leg through a first angle to change the angular orientation of the femur and tibia and to position the femur and tibia in a second orientation relative to each other, thereafter, making a second cut on the femur with at least a portion of the second cut in a second plane which extends at the first angle relative to the first plane, bending the leg through a second angle to change the angular orientation of the femur and tibia and to position the femur and tibia in a third orientation relative to each other, thereafter, making a third cut on the femur with at least a portion of the third cut in a third plane which extends at the second angle relative to the second plane, and maintaining the cam and follower in engagement during said steps of bending the leg.

88. A method as set forth in claim 87 further including the step of sequentially maintaining the femur and tibia in each of the first, second and third orientations relative to each other by retaining the cam and follower against movement relative to each other.

89. A method as set forth in claim 87 further including the step of distracting a knee interconnecting the femur and tibia prior to performance of said steps of making first, second and third cuts on the femur and maintaining the extent of distraction of the knee constant during said steps of bending the leg.

90. A method as set forth in claim 89 wherein said step of distracting the knee includes separating medial and lateral portions of end portions of the femur and tibia to different extents, said step of maintaining the extent of distraction of the knee constant during said steps of bending the leg includes maintaining the different extents of separation of the medial and lateral portions of the end portions of femur and tibia constant at the different extents of distraction.

91. A method as set forth in claim 87 further including the step of fixedly connecting a first mounting section with the first one of the femur and tibia at a plurality of locations along a longitudinal axis of the first one of the femur and tibia, said step of aligning a cam with the first one of the femur and tibia includes the step of fixedly securing the cam with the first mounting section after fixedly connecting the first mounting section with the first one of the femur and tibia, said method further including the step of fixedly connecting a second mounting section with the second one of the femur and tibia at a plurality of locations along a longitudinal axis of the second one of the femur and tibia, said step of aligning a follower with the second one of the femur and tibia includes the step of fixedly securing the follower with the second mounting section after fixedly connecting the second mounting section with the second one of the femur and tibia.

92. A method as set forth in claim 87 wherein said step of aligning a follower with a second one of the femur and tibia is performed prior to performance of said step of aligning a cam with a first one of the femur and tibia.

93. A method as set forth in claim 87 wherein said steps of aligning a cam with a first one of the femur and tibia and aligning a follower with a second one of the femur and tibia include locating a transverse axis of a knee interconnecting the femur and tibia, positioning the cam relative to the transverse axis of the knee, and positioning the follower relative to the transverse axis of the knee.

94. A method as set forth in claim 93 wherein said step of positioning the cam relative to the transverse axis of the knee includes moving the cam in a plane which extends generally perpendicular to the transverse axis of the knee, said step of positioning the follower relative to the transverse axis of the knee includes moving the follower in a plane which extends generally perpendicular to the transverse axis of the knee.

95. A method as set forth in claim 87 wherein said step of aligning the cam with a first one of the femur and tibia includes moving the leg and moving the cam relative to the first one of the femur and tibia.

96. A method as set forth in claim 87 further including the step of connecting a first mounting section with the first one of the femur and tibia, and connecting a second mounting section with the second one of the femur and tibia.

97. A method as set forth in claim 96 wherein said steps of aligning the cam with the first one of the femur and tibia and aligning the follower with the second one of the femur and tibia includes moving the cam and follower into abutting engagement after performing said step of connecting a first mounting section with the first one of the femur and tibia and after performing said step of connecting a second mounting section with the second one of the femur and tibia.

98. A method as set forth in claim 96 wherein said step of connecting the second mounting section with the second one of the femur and tibia includes engaging the tibial portion of the leg with a positioning member having a generally V-shaped cross sectional configuration to locate the second mounting section relative to the tibia.

99. A method as set forth in claim 96 wherein said step of connecting a first mounting section with the first one of the femur and tibia is performed with the cam disposed on the first mounting section, said step of connecting a second mounting section with a second one of the femur and tibia is performed with the follower disposed on the second mounting section, said method further including the step of moving the cam and follower relative to the first and second mounting sections after performing said steps of connecting the first mounting section with the first one of the femur and tibia and connecting the second mounting section with the second one of the femur and tibia.

100. A method of positioning a femur and tibia of a leg relative to each other during surgery, said method comprising the steps of distracting a knee joint interconnecting the femur and tibia, thereafter, positioning the leg in the first position with the femur and tibia in a first orientation relative to each other, making a first cut on the femur with at least a portion of the first cut in a first plane while the leg is in the first position, bending the leg from a first position to a second position, maintaining the extent of distraction of the knee joint constant during bending of the leg from the first position to the second position, said step of bending the leg from a first position to a second position including changing the angular orientation of the femur and tibia through a first angle and to position the femur and tibia in a second orientation relative to each other, thereafter, making a second cut on the femur with at least a portion of the second cut in a second plane which extends at the first angle relative to the first plane, bending the leg from the second position to a third position to change the angular orientation of the femur and tibia through a second angle and to position the femur and tibia in a third orientation relative to each other, maintaining the extent of distraction of the knee joint constant during bending of the leg from the second position to the third position, and, thereafter, making a third cut on the femur with at least a portion of the third cut in a third plane which extends at the second angle relative to the second plane.

101. A method as set forth in claim 100 wherein said step of distracting the knee joint includes separating end portions of the femur and tibia, said step of maintaining the extent of distraction of the knee joint constant during bending of the knee joint including maintaining the separation of the end portions of the femur and tibia constant during bending of the leg.

102. A method as set forth in claim 100 wherein said step of distracting a knee joint includes separating the femur and tibia by a first distance at a first portion of the knee joint and separating the femur and tibia by a second distance at a second portion of the knee joint, said first distance being greater than said second distance, said step of maintaining the extent of distraction of the knee joint constant during bending of the knee joint includes maintaining the first and second distances constant during bending of the knee joint.

103. A method as set forth in claim 100 wherein said step of distracting a knee joint includes moving one of a cam and cam follower relative to one of the femur and tibia while maintaining the position of another one of the cam and cam follower constant relative to another one of the femur and tibia.

104. A method as set forth in claim 100 further including the steps of aligning a cam with a first one of the femur and tibia, and aligning a follower with a second one of the femur and tibia, said step of maintaining the extent of distraction of the knee joint constant during bending of the knee joint including transmitting force between the cam and the cam follower during bending of the knee joint.

105. A method as set forth in claim 104 further including the step of maintaining the cam and cam follower in engagement during said step of bending the leg.

106. A method as set forth in claim 100 further including the steps of aligning a cam with a first one of the femur and tibia, and aligning a cam follower with a second one of the femur and tibia, said steps of aligning a cam with a first one of the femur and tibia and aligning a cam follower with a second one of the femur and tibia including moving one of the cam and cam follower relative to one of the femur and tibia while maintaining the position of another one of the cam and cam follower constant relative to another one of the femur and tibia.

107. A method as set forth in claim 100 further including the steps of positioning first and second cams adjacent to opposite sides of the knee, said step of positioning first and second cams adjacent to opposite sides of the knee including connecting a first mounting section with a first one of the femur and tibia, positioning first and second cam followers adjacent to opposite sides of the knee, said step of positioning first and second cam followers adjacent to opposite sides of the knee including connecting a second mounting section with a second one of the femur and tibia, said step of distracting the knee including transmitting force between the first and second cams and the first and second cam followers.

108. A method as set forth in claim 107 further including the step of maintaining the first cam and first cam follower in engagement during performance of said step of bending of the leg from the first position to the second position, and maintaining the second cam and second cam follower in engagement during bending of the leg from the first position to the second position.

109. A method as set forth in claim 100 further including the steps of connecting a first mounting section with a first one of the femur and tibia at a plurality of locations along a longitudinal axis of the first one of the femur and tibia, connecting a second mounting section with a second one of the femur and tibia at a plurality of locations along a longitudinal axis of the second one of the femur and tibia, thereafter, interconnecting the first and second mounting sections to retain the leg in the first position, disconnecting the first and second mounting sections to release the leg for movement from the first position after making the first cut, said step of bending the leg to a second position including effecting relative movement between the first and second mounting sections, and interconnecting the first and second mounting sections to retain the leg in the second position.

110. A method as set forth in claim 109 wherein said step of connecting a first mounting section with a first one of the femur and tibia is performed with the second mounting section disconnected from the first mounting section.

111. A method of positioning a femur and tibia of a leg relative to each other during surgery, said method comprising the steps of connecting a first mounting section with a first one of the femur and tibia at a plurality of locations along a longitudinal axis of the first one of the femur and tibia, connecting a second mounting section with a second one of the femur and tibia at a plurality of locations along a longitudinal axis of the second one of the femur and tibia, distracting a knee joint interconnecting the femur and tibia, thereafter, positioning the leg in a first position, said step of positioning the leg in a first position including effecting relative movement between the first and second mounting sections, interconnecting the first and second mounting sections to retain the leg in the first position, making a first cut on the femur while first and second mounting sections are interconnected with the leg in the first position, disconnecting the first and second mounting sections to release the leg for movement from the first position, thereafter, bending the leg from a first position to a second position, said step of bending the leg to a second position including effecting relative movement between the first and second mounting sections, interconnecting the first and second mounting sections to retain the leg in the second position, and making a second cut on the femur while the first and second mounting sections are interconnected with the leg in the second predetermined position, and maintaining the extent of distraction of the knee joint constant during bending of the leg.

112. A method as set forth in claim 111 wherein said step of connecting a first mounting section with a first one of the femur and tibia is performed with the second mounting section disconnected from the first mounting section.

113. A method as set forth in claim 111 wherein said step of distracting the knee joint includes separating end portions of the femur and tibia, said step of maintaining the extent of distraction of the knee joint constant during bending of the leg including maintaining the separation of the end portions of the femur and tibia constant during bending of the leg.

114. A method as set forth in claim 111 wherein said step of distracting a knee joint includes separating the femur and tibia by a first distance at a first portion of the knee joint and separating the femur and tibia by a second distance at a second portion of the knee joint, said first distance being greater than said second distance, said step of maintaining the extent of distraction of the knee joint constant during bending of the leg includes maintaining the first and second distances constant during bending of the leg.

115. A method as set forth in claim 111 wherein said step of distracting a knee joint includes moving one of a cam and cam follower relative to one of the femur and tibia while maintaining the position of another one of the cam and cam follower constant relative to another one of the femur and tibia.

116. A method as set forth in claim 111 further including the steps of aligning a cam with a first one of the femur and tibia, and aligning a follower with a second one of the femur and tibia, said step of maintaining the extent of distraction of the knee joint constant during bending of the leg including transmitting force between the cam and the cam follower during bending of the leg.

117. A method as set forth in claim 116 further including the step of maintaining the cam and cam follower in engagement during said step of bending the leg.

118. A method as set forth in claim 111 further including the steps of aligning a cam with a first one of the femur and tibia, and aligning a cam follower with a second one of the femur and tibia, said steps of aligning a cam with a first one of the femur and tibia and aligning a cam follower with a second one of the femur and tibia including moving one of the cam and cam follower relative to one of the femur and tibia while maintaining the position of another one of the cam and cam follower constant relative to another one of the femur and tibia.

119. A method as set forth in claim 111 further including the steps of positioning first and second cams adjacent to opposite sides of the knee, positioning first and second cam followers adjacent to opposite sides of the knee, said step of distracting the knee including transmitting force from the first and second cams to the first one of the femur and tibia through the first mounting section and transmitting force from the first and second cam followers to the second one of the femur and tibia through the second mounting section.

120. A method as set forth in claim 119 further including the step of maintaining the first cam and first cam follower in engagement during performance of said step of bending of the leg from the first position to the second position, and maintaining the second cam and second cam follower in engagement during bending of the leg from the first position to the second position.

121. An apparatus for use in positioning the femur and tibia of a leg relative to each other during surgery, said apparatus comprising a first section, means for connecting said first section with the femur, a second section, means for connecting said second section with the tibia, first means for defining a first plurality of index locations disposed in a first array, said first means being disposed adjacent to a side of the leg and being connected with a first one of said first and second sections, each index location of said first plurality of index locations corresponding to a different one of a plurality of predetermined orientations of the femur and tibia relative to each other, means for adjusting the location of said first plurality of index locations relative to the first one of said first and second sections along a first axis and along a second axis which extends perpendicular to the first axis, and first retainer means disposed adjacent to the side of the leg for engaging each of the index locations in said first plurality of index locations in turn, said first retainer means being connected with a second one of said first and second sections.

122. An apparatus as set forth in claim 121 wherein said means for connecting said first section with the femur includes a plurality of members which engage the femur at a plurality of locations spaced apart along a longitudinal axis of the femur, said means for connecting said second section with the tibia including a plurality of members which engage the tibia at a plurality of locations spaced apart along a longitudinal axis of the tibia.

123. An apparatus as set forth in claim 121 wherein said first and second sections are movable relative to each other during flexion or extension of the leg to vary a distance measured along the longitudinal axes of the femur and tibia and extending between said means for connecting said first section with the femur and said means for connecting said second section with the tibia.

124. An apparatus as set forth in claim 121 wherein said first means for defining a first plurality of index locations includes means for defining a plurality of index locations which are spaced unequal distances apart in a noncircular arcuate array having a configuration which is a function of the relative movement between the femur and tibia during bending of the leg.

125. An apparatus as set forth in claim 121 further including means for effecting distraction of a knee joint interconnecting the femur and tibia, said means for effecting distraction of the knee joint including means for moving end portions of the femur and tibia away from each other and for maintaining the extent of separation between end portions of the femur and tibia constant during flexion or extension of the leg.

126. An apparatus as set forth in claim 121 further including means connected with said first and second sections for maintaining a distance separating end portions of the femur and tibia constant during flexion or extension of the leg during surgery.

127. An apparatus as set forth in claim 126 wherein said means for maintaining a distance separating end portions of the femur and tibia constant during flexion or extension of the leg includes means for effecting distraction of a knee joint interconnecting the femur and tibia.

128. A method of positioning a femur and tibia of a leg relative to each other during surgery, said method comprising the steps of connecting a first mounting section with a first one of the femur and tibia, connecting a second mounting section with a second one of the femur and tibia, moving a first cam connected with the first mounting section and a first follower connected with the second mounting section into engagement, said step of moving a first cam and first follower into engagement being performed with the first cam and first follower disposed adjacent to a first side of the leg, moving a second cam connected with the first mounting section and a second follower connected with the second mounting section into engagement, said step of moving a second cam and a second follower into engagement being performed with the second cam and second follower adjacent to a second side of the leg, thereafter, bending the leg, moving the first cam and first follower relative to each other while maintaining the first cam and first follower in engagement with each other during performance of said step of bending the leg, and moving the second cam and second follower relative to each other while maintaining the second cam and second follower in engagement with each other during performance of said step of bending the leg.

129. A method as set forth in claim 128 further including the steps of distracting a knee joint interconnecting the femur and tibia, thereafter, performing said step of bending the leg, and maintaining the extent of distraction of the knee joint constant during performance of said step of bending the leg.

130. A method as set forth in claim 129 wherein said step of maintaining the extent of distraction of the knee joint constant during bending the leg includes transmitting force between the first cam and first cam follower and transmitting force between the second cam and second cam follower during performance of said step of bending the leg.

131. An apparatus for use in positioning the femur and tibia of a leg relative to each other during surgery, said apparatus comprising a first section, means for connecting said first section with the femur, a second section, means for connecting said second section with the tibia, first cam means having a configuration which is a function of the configuration of at least a portion of an end portion of one of the femur and tibia, said first cam means being disposed adjacent to a first side of the leg and being connected with a first one of said first and second sections, first follower means for engaging said first cam means during bending of the leg, said first follower means being disposed adjacent to the first side of the leg and being connected with a second one of said first and second sections, second cam means having a configuration which is a function of the configuration of at least a portion of an end portion of one of the femur and tibia, said second cam means being disposed adjacent to a second side of the leg and being connected with the first one of said first and second sections, and second follower means for engaging said second cam means during bending of the leg, said second follower means being disposed adjacent to the second side of the leg and being connected with the second one of said first and second sections.

132. An apparatus as set forth in claim 131 wherein said means for connecting said first section with the femur includes a plurality of members which engage the femur at a plurality of locations spaced apart along a longitudinal axis of the femur, said means for connecting said second section with the tibia including a plurality of members which engage the tibia at a plurality of locations spaced apart along a longitudinal axis of the tibia.

133. An apparatus as set forth in claim 132 wherein said first and second sections are movable relative to each other in such a manner as to vary a distance measured along the longitudinal axes of the femur and tibia and extending between said members which engage the femur and said members which engage the tibia during flexion or extension of the leg.

134. An apparatus as set forth in claim 131 further including means for adjusting the location of said first cam means relative to the first one of said first and second sections along a first axis and along a second axis which extends perpendicular to the first axis and means for adjusting the location of said second cam means reactive to the first one of said first and second sections along a third axis and along a fourth axis which extends perpendicular to the third axis.

135. An apparatus as set forth in claim 131 wherein said means for connecting said first section with the femur includes means for mounting said first section on the femur for movement therewith, said means for connecting said second section with the tibia including means for mounting said second section on the tibia for movement therewith.

136. An apparatus as set forth in claim 131 wherein at least one of said first cam means and said first follower means and wherein at least one of said second cam means and said second follower means are adjustable to move portions of the femur and tibia away from each other.

137. An apparatus as set forth in claim 131 wherein at least one of said first cam means and first follower means is adjustable to move medial portions of the femur and tibia away from each other through a first distance and at least one of said second cam means and second follower means is adjustable to move lateral portions of the femur and tibia away from each other through a second distance which is different than the first distance.

* * * * *

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

Column 20, lines 39 through 61, rewrite claims 2 through 4 as follows:

2. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, index means for retaining said first and second sections in any one of a plurality of predetermined orientations relative to each other to retain the femur and tibia in any one of the plurality of predetermined orientations relative to each other and for releasing said first and second sections for movement relative to each other from one of said predetermined orientations to another of said

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

predetermined orientations, and a cam surface connected with one of said first and second sections and a follower connected with another of said first and second sections and engageable with said cam surface during flexion or extension of the leg, said cam surface having a configuration which is a function of the relative movement between the femur and tibia during flexion or extension of the leg.

3. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, and index means for retaining said first and second sections

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

in any one of a plurality of predetermined orientations relative to each other to retain the femur and tibia in any one of the plurality of predetermined orientations relative to each other and for releasing said first and second sections for movement relative to each other from one of said predetermined orientations to another of said predetermined orientations, said means for mounting said second section on the tibia includes means for fixedly securing the second section to the tibia at a mounting location, said second section and mounting location being movable relative to said first section along a longitudinal axis of the tibia during flexion or extension of the leg.

4. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

for movement therewith relative to said first section and the femur, said first and second sections being movable relative to each other during flexion or extension of the leg with said first and second sections mounted on the leg, index means for retaining said first and second sections in any one of a plurality of predetermined orientations relative to each other to retain the femur and tibia in any one of the plurality of predetermined orientations relative to each other and for releasing said first and second sections for movement relative to each other from one of said predetermined orientations to another of said predetermined orientations, said index means includes adjustable means connected with one of said first and second sections for defining a plurality of index locations, and means for use in positioning said adjustable means relative to said one of said first and second sections to locate said plurality of index locations relative to said one of said first and second sections.

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

Column 21, line 8, through column 22, line 3, rewrite claims 7 through 12 as follows:

7. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, and index means for retaining said first and second sections in any one of a plurality of predetermined orientations relative to each other to retain the femur and tibia in any one of the plurality of predetermined orientations relative to each other and for releasing said first and second

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

sections for movement relative to each other from one of said predetermined orientations to another of said predetermined orientations, said means for mounting said first section on the femur includes means for engaging a first side of the femur at a plurality of locations spaced apart in an axial direction along the first side of the femur and means for engaging a second side of the femur at a plurality of locations spaced apart in an axial direction along the second side of the femur, said means for mounting said second section on the tibia includes means for engaging a first side of the tibia at a plurality of locations spaced apart in an axial direction along a first side of the tibia and means for engaging a second side of the tibia at a plurality of locations spaced apart in an axial direction along the second side of the tibia.

8. An apparatus for use in positioning the femur and tibia of a leg in a plurality of predetermined orientations relative to each other during surgery, said apparatus

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, and index means for retaining said first and second sections in any one of a plurality of predetermined orientations relative to each other to retain the femur and tibia in any one of the plurality of predetermined orientations relative to each other and for releasing said first and second sections for movement relative to each other from one of said predetermined orientations to another of said predetermined orientations, said index means includes a plurality of index locations connected with one of said first and second sections and disposed in a noncircular arcuate array and means connected with the other of said

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

first and second sections for engaging each of the index locations in turn.

9. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, and index means for retaining said first and second sections in any one of a plurality of predetermined orientations relative to each other to retain the femur and tibia in any one of the plurality of predetermined orientations relative to each other and for releasing said first and second sections for movement relative to each other from one of

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

said predetermined orientations to another of said predetermined orientations, said index means includes a first plurality of index locations disposed adjacent to a first side of the leg, each index location of said first plurality of index locations corresponding to a different orientation of the femur and tibia relative to each other, a second plurality of index locations disposed adjacent to a second side of the leg opposite from the first side of the leg, each index location of said second plurality of index locations corresponding to an orientation of the femur and tibia which is the same as an index location of the first plurality of index locations, first retainer means for engaging each of the index locations in the first plurality of index locations in turn, and second retainer means for engaging an index location in the second plurality of index locations which corresponds to an orientation of the femur and tibia which is the same as an index location engaged by said first retainer means.

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

10. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, and index means for retaining said first and second sections in any one of a plurality of predetermined orientations relative to each other to retain the femur and tibia in any one of the plurality of predetermined orientations relative to each other and for releasing said first and second sections for movement relative to each other from one of said predetermined orientations to another of said predetermined orientations, said index means includes a plurality of spaced apart openings connected with one of

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

said first and second sections and means for engaging each of said openings in turn connected with another of said first and second sections.

11. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the leg with said first and second sections mounted on the leg, index means for retaining said first and second sections in any one of a plurality of predetermined orientations relative to each other to retain the femur and tibia in any one of the plurality of predetermined orientations relative to each other and for releasing said first and second

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

sections for movement relative to each other from one of said predetermined orientations to another of said predetermined orientations, and means for effecting distraction of a knee joint interconnecting the femur and tibia, said means for effecting distraction and including means for separating end portions of the femur and tibia and for maintaining the extent of separation of the end portions of the femur and tibia constant during flexion or extension of the leg.

12. An apparatus for use in positioning the femur and tibia of a leg in a plurality of predetermined orientations relative to each other during surgery, said apparatus comprising a first section, means for mounting said first section on the femur for movement therewith, a second section, means for mounting said second section on the tibia for movement therewith relative to said first section and the femur, said first and second sections being movable relative to each other during flexion or extension of the

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

leg with said first and second sections mounted on the leg, index means for retaining said first and second sections in any one of a plurality of predetermined orientations relative to each other to retain the femur and tibia in any one of the plurality of predetermined orientations relative to each other and for releasing said first and second sections for movement relative to each other from one of said predetermined orientations to another of said predetermined orientations, a first cam surface disposed adjacent to a first side of the leg, said first cam surface having a configuration which is a function of the configuration of at least a portion of an end portion of one of the femur and tibia, a second cam surface disposed adjacent to a second side of the leg opposite from the first side of the leg, said second cam surface having a configuration which is a function of the configuration of at least a portion of an end portion of one of the femur and tibia, a first cam follower disposed adjacent to the first side of the leg and engageable with the first cam surface

UNITED STATES PATENT AND TRADEMARK OFFICE
CERTIFICATE OF CORRECTION

PATENT NO. : 5,514,143
DATED : May 7, 1996
INVENTOR(S) : PETER M. BONUTTI and GARY E. ZITZMANN It is certified that error appears in the above-indentified patent and that said Letters Patent is hereby corrected as shown below:

during flexion or extension of the leg, and a second cam follower disposed adjacent to the second side of the leg and engageable with the second cam surface during flexion or extension of the leg.

Signed and Sealed this

Twenty-fourth Day of December, 1996

Attest:

BRUCE LEHMAN

Attesting Officer     Commissioner of Patents and Trademarks